US011401304B2

(12) United States Patent
Urban et al.

(10) Patent No.: US 11,401,304 B2
(45) Date of Patent: Aug. 2, 2022

(54) CYCLIC NTCP-TARGETING PEPTIDES AND THEIR USES AS ENTRY INHIBITORS

(71) Applicant: Ruprecht-Karls-Universität Heidelberg, Heidelberg (DE)

(72) Inventors: Stephan Urban, Neustadt/Weinstrasse (DE); Yi Ni, Eppelheim (DE); Walter Mier, Bensheim (DE)

(73) Assignee: RUPRECHT-KARLS-UNIVERSITÄT HEIDELBERG, Heidelberg (DE)

( * ) Notice: Subject to any disclaimer, the term of this patent is extended or adjusted under 35 U.S.C. 154(b) by 0 days.

(21) Appl. No.: 15/780,129

(22) PCT Filed: Dec. 15, 2016

(86) PCT No.: PCT/EP2016/081117
§ 371 (c)(1),
(2) Date: May 30, 2018

(87) PCT Pub. No.: WO2017/102906
PCT Pub. Date: Jun. 22, 2017

(65) Prior Publication Data
US 2018/0354993 A1 Dec. 13, 2018

(30) Foreign Application Priority Data

Dec. 16, 2015 (EP) ..................................... 15200494

(51) Int. Cl.
| | | |
|---|---|---|
| C07K 14/00 | (2006.01) |
| C07K 14/005 | (2006.01) |
| A61K 51/08 | (2006.01) |
| A61K 49/00 | (2006.01) |
| C07K 7/64 | (2006.01) |
| C07K 7/50 | (2006.01) |
| C07K 7/06 | (2006.01) |
| C07K 7/08 | (2006.01) |
| A61P 31/20 | (2006.01) |
| A61K 38/00 | (2006.01) |

(52) U.S. Cl.
CPC ........ C07K 14/001 (2013.01); A61K 49/0056 (2013.01); A61K 51/088 (2013.01); A61P 31/20 (2018.01); C07K 7/06 (2013.01); C07K 7/08 (2013.01); C07K 7/50 (2013.01); C07K 7/64 (2013.01); C07K 14/005 (2013.01); A61K 38/00 (2013.01); C12N 2730/10122 (2013.01); C12N 2730/10133 (2013.01); C12N 2730/10134 (2013.01); C12N 2730/10141 (2013.01); Y02A 50/30 (2018.01)

(58) Field of Classification Search
None
See application file for complete search history.

(56) References Cited

FOREIGN PATENT DOCUMENTS

| | | | | |
|---|---|---|---|---|
| CN | 103402545 A | 11/2013 | | |
| CN | 104781274 A | 7/2015 | | |
| JP | 2014506574 A | 3/2014 | | |
| JP | 2014101274 A | 6/2014 | | |
| JP | 2015120657 A | 7/2015 | | |
| WO | WO-2004058807 A2 * | 7/2004 | ........... | C07K 14/005 |
| WO | 2009092612 A1 | 7/2009 | | |
| WO | WO-2009092611 A1 * | 7/2009 | ................ | A61P 1/16 |
| WO | 2012/107579 A1 | 8/2012 | | |
| WO | 2012107579 A1 | 8/2012 | | |
| WO | WO-2012107579 A1 * | 8/2012 | ........... | A61K 51/088 |
| WO | 2014/072524 A1 | 5/2014 | | |
| WO | 2014103203 A1 | 7/2014 | | |
| WO | 2014115229 A1 | 7/2014 | | |

OTHER PUBLICATIONS

Thakkar et al. "Global Analysis of Peptide Cyclization Efficiency" ACS Comb. Sci. 15:120-129. (Year: 2013).*
Schulze et al. "Fine Mapping of Pre-S Sequence Requirements for Hepatitis B Virus Large Envelope Protein-Mediated Receptor Interaction" J. Virol. 84:1989-2000. (Year: 2010).*
Wang et al. "Synthesis of small cyclic peptides containing the disulfide bond" ARKIVOC 2006 (xi):1-7. (Year: 2006).*
Davies J "The Cyclization of Peptides and Depsipeptides" J. Peptide Sci. 9:471-501. (Year: 2003).*
Urban et al. "Strategies to Inhibit Entry of HBV and HDV Into Hepatocytes" Gastroenterology 147:48-64. (Year: 2014).*
Schieck et al. "Hepatitis B Virus Hepatotropism is Mediated by Specific Receptor Recognition in the Liver and Not Restricted to Susceptible Hosts" Hepatology 58:43-53. (Year: 2013).*
Brown, S.E., et al., "Determination of the Affinity of Antibodies to Hepatitis B Surface Antigen in Human Sera." Journal of Immunological Methods, 1984, 72: 41-48.
Camerino, M.A., et al., "Computer-assisted design of cyclic peptides and peptidomimetics." Chemistry Today, 2008, 26(5): 1-4.
Guarracino, D.A., "Wheel of Fortune—Cyclic Peptides Hit the Mimetic Jackpot: Current Syntheses, Uses and Roles for Cyclic Peptide Mimetics." Current Chemical Biology, 2015, 9: 36-52.
Kennedy, R.C., et al., "Inhibition of a Common Human Anti-Hepatitis B Surface Antigen Idiotype by a Cyclic Synthetic Peptide." Journal of Virology, May 1983, 46(2): 653-655.
Kim, D., et al., "An anti-viral peptide derived from the preS1 surface protein of hepatitis B virus" BMB reports, 2008, 41(9): 640-644.

(Continued)

*Primary Examiner* — Sudhakar Katakam
*Assistant Examiner* — Zachary J Miknis
(74) *Attorney, Agent, or Firm* — Saliwanchik, Lloyd & Eisenschenk

(57) ABSTRACT

The present invention relates to cyclic NTCP targeting peptides which are preS-derived peptides of hepatitis B virus (HBV). The present invention further relates to pharmaceutical compositions comprising at least one cyclic peptide. The present invention further relates to medical uses of said cyclic peptides and the pharmaceutical compositions, such as in the diagnosis, prevention and/or treatment of a liver disease or condition, and/or in the inhibition of HBV and/or HDV infection. The present invention further relates to methods of diagnosis, prevention and/or treatment of a liver disease or condition and/or the inhibition of HBV and/or HDV infection.

8 Claims, 9 Drawing Sheets

Specification includes a Sequence Listing.

(56) References Cited

OTHER PUBLICATIONS

Levengood, M.R., Van Der Donk, W.A., "Use of Lantibiotic Synthetases for the Preparation of Bioactive Constrained Peptides." Bioorg Med Chem Lett., May 2008, 18(10): 3025-3028.

Somiya, M., et al., "Intracellular trafficking of bio-nanocapsule-liposome complex: Identification of fusogenic activity in the pre-S1 region of hepatitis B virus surface antigen L protein." Journal of Controlled Release, 2015, 212: 10-18.

Urban, S., et al., "Strategies to Inhibit Entry of HBV and HDV Into Hepatocytes." Gastroenterology, 2014, 147: 48-64.

Akcan and Criak, Chapter 5, Conotoxin-based Leads in Drug Design, Peptide Drug Discovery and Development: Translational Research in Academia and Industry, 1st Edition, Ed. Castanho and Santos, Wiley-VCH Verlag GmbH, 2011.

Andreotti, Giuseppina et al. "Structural Determinants of Salmon Calcitonin Bioactivity" Journal of Biological Chemistry 281 (34):24193-24203, Aug. 25, 2006.

Atkinson, R. Andrew et al. "Structural and Dynamic Characterization of w-Conotoxin MVIIA: The Binding Loop Exhibits Slow Conformational Exchange," Biochemistry 39:3908-3919, 2000.

Jensen, Jonas E. et al. "Cyclisation Increases the Stability of the Sea Anemone Peptide APETx2 but Decreases its Activity at Acid-Sensing Ion channel 3," Mar. Drugs 10:1511-1527, Jul. 16, 2012.

Kazantzis, Athanasios et al. "Conformationally constrained human calcitonin (hCt) analogues reveal a critical role of sequence 17-21 for the oligomerization state and bioactivity of hCt," Eur. J Biochem 269:780-791, 2002.

Kim, Do-Hyoung et al. "An anti-viral peptide derived from the preS1 surface protein of hepatitis B virus," BMB Reports, Sep. 30, 2008, pp. 640-644.

Rose, John P. et al. "Crystal structure of the neurophysin-oxytocin complex," Nature Structural Biology, 3 (2):163-169, Feb. 2, 1996.

Tapeinou, Anthi et al. "Cyclic Peptides on a Merry-Go-Round; Towards Drug Design," Peptide Science, 104 (5):453-461,2015. Note* p. 455, Table 1 is highlighted to show the active sites of the four cyclised peptides.

Communication of Notice of Opposition issued by the European Patent Office regarding parallel European Patent Application No. EP 16822406.1/Patent No. EP 3389691.

Initial Office Action issued by the Chinese Patent Office in corresponding Application No. 201680074585.9, dated Jun. 8, 2021 with English translation.

* cited by examiner

A covalently bridged cyclic derivative of Myrcludex B shows inhibitory potential.

cyclo-Myr-preS2-48   SEQ ID NO. 25

CYCLIC NTCP-TARGETING PEPTIDES AND THEIR USES AS ENTRY INHIBITORS

CROSS REFERENCE TO RELATED APPLICATIONS

This application is a National Stage Application of International Application Number PCT/EP2016/081117, filed Dec. 15, 2016; which claims priority to European Patent Application No. 15 200 494.1, filed Dec. 16, 2015.

The Sequence Listing for this application is labeled "SeqList-17May18-ST25.txt", which was created on May 17, 2018, and is 23 KB. The entire content is incorporated herein by reference in its entirety.

The present invention relates to cyclic NTCP targeting peptides which are preS-derived peptides of hepatitis B virus (HBV). The present invention further relates to pharmaceutical compositions comprising at least one cyclic peptide. The present invention further relates to medical uses of said cyclic peptides and the pharmaceutical compositions, such as in the diagnosis, prevention and/or treatment of a liver disease or condition, and/or in the inhibition of HBV and/or HDV infection. The present invention further relates to methods of diagnosis, prevention and/or treatment of a liver disease or condition and/or the inhibition of HBV and/or HDV infection.

BACKGROUND OF THE INVENTION

Today, about 2 billion people carry serological markers of HBV. About 400 million of them are chronically infected with HBV. According to the center of disease control (CDC) 15-25% of chronically HBV infected people are prone to develop hepatocellular carcinoma (HCC) within a decade if they do not receive appropriate treatment (Shephard et al., 2006). HBV-related HCC has a poor prognosis and HBV has therefore been classified by the world health organization (WHO) as the most important naturally occurring human carcinogen. Despite the existence of a prophylactic vaccine, the number of infections will rise in the upcoming decades due to the increasing world population and the limitation of prophylaxis in the poor countries.

HBV is primarily transmitted via the parenteral route. 90-95% of the acutely infected, immune competent individuals clear the virus, thereby gaining life-long immune protection. About 5-10% of infected people develop chronic Hepatitis B (300,000-500,000 persons in Germany). In contrast, in high endemic areas, particularly Central Africa and Eastern Asia, the main mode of transmission is perinatal from mother to child. Unfortunately, infection of not fully immunocompetent children results in a 90-98% chronic course of the disease. Hepatitis B-related HCC is therefore the most common malignancy in many of these countries.

Currently approved therapeutic regiments for the treatment of chronic hepatitis B virus (HBV) infections either address replication steps of the viral genome after an already established infection (Lamivudine, Adefovir, Entecavir, Tenofovir) or act as modulators of the immune system (interferon alpha). Unfortunately, only 10-25% of the patients preserve a sustained virological response upon such therapies. It is therefore of utmost importance to develop novel therapeutics that target so far unaffected replication steps (e.g. virus entry) that may help to eliminate the virus and cure infection.

Despite of the availability of a prophylactic vaccine and reverse transcriptase (RT) inhibitors, the number of HBV-infected people and the number of HBV-related deaths worldwide (presently about 500,000 per year) is increasing. About two thirds of primary liver cancers are attributable to persistent HBV infection (Chan & Sung, 2006).

Specific inhibition of virus entry is an attractive therapeutic concept to control and eventually eliminate acute and chronic infections by different viruses. Entry inhibition has curative potential as it has recently been demonstrated in a mouse model for HCV infection (Mailly et al., 2014)

The human hepatitis B virus (HBV) is a member of the hepadnaviridae. Hepadnaviruses are the smallest enveloped DNA viruses which replicate via reverse transcription of a pgRNA intermediate. During assembly the nucleocapsid acquires three viral envelope proteins termed large (L), middle (M) and small (S). They are encoded in one open reading frame and share the S-domain which is required for membrane anchoring. In addition to the S-domain, M contains an N-terminal hydrophilic extension of 55 amino acids (preS2), while L is further extended by 107, 117 or 118 amino acids (genotype-dependent) termed preS1 (Urban et al., 2014). The hepatitis D virus (HDV) is a satellite virusoid utilizing the HBV envelope proteins for entry into hepatocytes. The myristoylated preS1-domain of L is known to play the key role in HBV and HDV infectivity.

The inventors have previously identified HBV L-protein derived lipopeptides that block HBV and HDV infection of PHH and HepaRG cells (Gripon et al., 2005, Schulze et al., 2010, WO 2009/092611 A1). They are derived from the N-terminal 47 amino acids of the preS1-domain of HBV genotype D (HBVpreS/2-48$^{myr}$) and include the naturally occurring modification with myristic acid.

In WO 2009/092612 and WO 2012/107579, whose contents are incorporated herewith by reference in its entirety, the inventors describe hydrophobic modified preS-derived peptides of HBV and their use as vehicles for the specific delivery of compounds to the liver.

The inventors have furthermore previously identified the receptor responsible for the binding of these HBV L-protein derived lipopeptides, namely sodium taurocholate co-transporting polypeptide (NTCP/SLC10A1). (WO 20014/072526, WO 2014/072524 and WO 2015/014830). See also Ni et al. (2014) and Yan et al. (2012).

The present invention aims to improve the methods and means for the inhibition of NTCP as a HBV and HDV receptor and NTCP-mediated transport of natural substrates and xenobiotics.

It is, thus, an objective of the present invention to provide improved means and methods for the diagnosis, prevention and/or treatment of liver diseases, such as liver diseases related to NTCP-mediated transport.

The present invention further aims to improve the methods and means for the inhibition, prevention and/or treatment of HBV-infection and other HBV-related diseases as present in the prior art and it is, thus, an objective of the present invention to provide improved methods and means which allow for a targeted and effective inhibition, prevention and/or treatment of HBV infection and related diseases.

It is a further objective of the present invention to provide improved means and methods for the inhibition, prevention and/or treatment of HDV infection and HDV-related diseases.

SUMMARY OF THE INVENTION

According to the present invention this object is solved by providing a cyclic peptide of the general formula I $$(X)_m-P-(Y)_n \qquad (I)$$

wherein
P is the amino acid sequence NPLGFXaaP (SEQ. ID NO: 1), with Xaa being F or L,
X is an amino acid sequence having a length of m amino acids,
wherein m is 0 or at least 1;
Y is an amino sequence having a length of n amino acids,
wherein n is 0 or at least 1;
and wherein m+n is 0 or at least 1;
or a pharmaceutically acceptable salt thereof.

According to the present invention this object is solved by providing a pharmaceutical composition comprising
(i) at least one cyclic peptide of the present invention,
(ii) optionally, a pharmaceutically acceptable carrier and/or excipient.

According to the present invention this object is solved by providing the cyclic peptide of the present invention or the pharmaceutical composition of the present invention for use in medicine.

According to the present invention this object is solved by providing the cyclic peptide of the present invention or the pharmaceutical composition of the present invention for use in the inhibition of HBV and/or HDV infection.

According to the present invention this object is solved by providing the cyclic peptide of the present invention or the pharmaceutical composition of the present invention for use in the prevention of a primary HBV and/or HDV infection.

According to the present invention this object is solved by providing the cyclic peptide of the present invention or the pharmaceutical composition of the present invention for use as HBV and/or HDV entry inhibitors According to the present invention this object is solved by providing the cyclic peptide of the present invention or the pharmaceutical composition of the present invention for use in the diagnosis, prevention and/or treatment of a liver disease or condition.

According to the present invention this object is solved by providing the cyclic peptide of the present invention or the pharmaceutical composition of the present invention for use in the diagnosis, prevention and/or treatment of a cardiovascular disease (CVD).

According to the present invention this object is solved by a method for the inhibition of HBV and/or HDV infection and/or the prevention of a primary HBV and/or HDV infection, comprising the administration of a therapeutically effective amount of a cyclic peptide of the present invention or a pharmaceutical composition of the present invention.

According to the present invention this object is solved by a method for the diagnosis, prevention and/or treatment of a liver disease or condition, comprising the administration of a therapeutically effective amount of a cyclic peptide of the present invention or a pharmaceutical composition of the present invention.

According to the present invention this object is solved by a method for the diagnosis, prevention and/or treatment of a cardiovascular disease (CVD), comprising the administration of a therapeutically effective amount of a cyclic peptide of the present invention or a pharmaceutical composition of the present invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "7 to 49" should be interpreted to include not only the explicitly recited values of 4 to 19, but also include individual values and sub-ranges within the indicated range. Thus, included in this numerical range are individual values such as 7, 8, 9, 10, 11, 12, 13, 14, 15, 16 . . . 37, 38, 39, 40, 41, 42, 43, 44, 45, 46, 47, 48, 49, and sub-ranges such as from 7 to 10, from 10 to 15, from 15 to 25, from 28 to 39, from 35 to 47, from 35 to 49 etc. This same principle applies to ranges reciting only one numerical value, such as "at least 1 or "at least one amino acid". Furthermore, such an interpretation should apply regardless of the breadth of the range or the characteristics being described.

Cyclic NTCP Targeting Peptides

As outlined above, the present invention provides cyclic peptides.

Said cyclic peptides are preS-derived peptides of hepatitis B virus (HBV).

A cyclic peptide of the present invention has the general formula I

$(X)_m—P—(Y)_n$         (I)

wherein
P is the amino acid sequence NPLGFXaaP (SEQ. ID NO: 1), with Xaa being F or L,
X is an amino acid sequence having a length of m amino acids,
wherein m is 0 or at least 1;
Y is an amino sequence having a length of n amino acids,
wherein n is 0 or at least 1;
and wherein m+n is 0 or at least 1;
or a pharmaceutically acceptable salt thereof.

Preferably, m+n is 0 to 42,
and/or wherein m=0 to 8 and/or n=0 to 34, provided that m+n is 0 or at least 1.

In an embodiment with m+n=0, the peptide has a length of/contains 7 amino acids (namely P); m+n=1, the peptide has a length of/contains 8 amino acids;
m+n=2, the peptide has a length of/contains 9 amino acids;
m+n=3, the peptide has a length of/contains 10 amino acids;
m+n=4, the peptide has a length of/contains 11 amino acids;
m+n=5, the peptide has a length of/contains 12 amino acids;
m+n=6, the peptide has a length of/contains 13 amino acids;
m+n=7, the peptide has a length of/contains 14 amino acids;
m+n=8, the peptide has a length of/contains 15 amino acids;
m+n=15, the peptide has a length of/contains 22 amino acids;
m+n=40, the peptide has a length of/contains 47 amino acids;

m+n=42, the peptide has a length of/contains 49 amino acids.

Cyclization

The cyclic peptides of the present invention can be cyclized in different ways, preferably
(a) via thiol oxidation (disulfide bridge formation) of two cysteines (C) comprised in the peptide,
   such as via a C at or near the N-terminus and a C at or near the C-terminus (of the peptide sequence before cyclization);
(b) amide condensation of two amino acid side chains (lactam),
   such as via a lysine (K) side chain and an aspartic acid (D) side chain,
      such as
         via a K side chain at or near the N-terminus and a D side chain at or near the C-terminus (of the peptide sequence before cyclization);
(c) via head-to-tail cyclization,
   such as
      via a lysine (K) at the N-terminus and the C-terminus (of the peptide sequence before cyclization),
      via the N-terminus, i.e. the amino group of the N-terminal amino acid and the C-terminus, i.e. carboxyl group of the C-terminal amino acid (of the peptide sequence before cyclization),
(d) via backbone cyclization,
(e) via thioether formation,
and/or
(f) via hydrogen bond formation and/or bond-forming derivatives of amino acids,
   such as amino acids forming a tryptophan zipper.

Preferably, the cyclic peptides of the present invention do not comprise peptides which are cyclized within the amino acid sequence of P (i.e. within the pharmacophore of 7 amino acids, of SEQ ID NO. 1 (NPLGFXaaP with Xaa=F or L)). i.e. via amino acid side chains of P.

However, the P sequence can be cyclized via head-to-tail cyclization.

For example, in one embodiment, the cyclic peptide comprises P NPLGFXaaP with Xaa=F, i.e. NPLGFFP (SEQ. ID NO: 2), and m and n are each 0. The peptide is cyclized via head-to-tail cyclization via the N-terminus, i.e. amino group of the N-terminal asparagine (N) and the C-terminus, i.e. carboxyl group of the C-terminal amino acid proline (P).

In one embodiment the cyclic peptide comprises P NPLGFXaaP with Xaa=F, i.e. NPLGFFP (SEQ. ID NO: 2), and X=Cys and Y=Cys, m and n are each 1. The peptide can be cyclized via thiol oxidation (disulfide bridge formation) of the two cysteines (C).

In one embodiment the cyclic peptide comprises P NPLGFXaaP with Xaa=F, i.e. NPLGFFP (SEQ. ID NO: 2), and X=Cys and Y=Asp-Cys, m=1 and n=2. The peptide can be cyclized via thiol oxidation (disulfide bridge formation) of the two cysteines (C).

In one embodiment the cyclic peptide comprises P NPLGFXaaP with Xaa=F, i.e. NPLGFFP (SEQ. ID NO: 2), and X=Cys and Y=His-Asp-Cys, m=1 and n=3. The peptide can be cyclized via thiol oxidation (disulfide bridge formation) of the two cysteines (C).

In one embodiment the cyclic peptide comprises P NPLGFXaaP with Xaa=F, i.e. NPLGFFP (SEQ. ID NO: 2), and X=Cys-Pro and Y=Asp-Cys, m=2 and n=2. The peptide can be cyclized via thiol oxidation (disulfide bridge formation) of the two cysteines (C).

In one embodiment the cyclic peptide comprises P NPLGFXaaP with Xaa=F, i.e. NPLGFFP (SEQ. ID NO: 2), and X=Cys-Pro and Y=His-Asp-Cys, m=2 and n=3. The peptide can be cyclized via thiol oxidation (disulfide bridge formation) of the two cysteines (C).

In one embodiment the cyclic peptide comprises the Myrcludex B sequence with P NPLGFXaaP with Xaa=F, i.e. NPLGFFP (SEQ. ID NO: 2), and m=7 and n=33. The peptide can be cyclized via head-to-tail cyclization via the N-terminus, i.e. the amino group of the N-terminal glycine (G) and the C-terminus, i.e. carboxyl group of the C-terminal amino acid glycine (G).

In one embodiment the cyclic peptide comprises the Myrcludex B sequence with P NPLGFXaaP with Xaa=F, i.e. NPLGFFP (SEQ. ID NO: 2), and two additional cysteines, such that m=8 and n=34. The peptide can be cyclized via thiol oxidation (disulfide bridge formation) of the two cysteines (C).

In other embodiments, the cyclic peptides comprise P NPLGFXaaP with Xaa=L, i.e. NPLGFLP (SEQ. ID NO: 3), respectively, as well as optionally the further additional amino acids, as described above.

Hydrophobic Modification

In a preferred embodiment, the cyclic peptide of the present invention is hydrophobically modified, i.e. it carries at least one covalently attached hydrophobic modification.

The position of the hydrophobic modification(s) can vary within the peptide sequence. Preferably, the hydrophobic modification(s) is/are at amino acid side chain(s) of X and/or Y. In one embodiment, the hydrophobic modification(s) is/are at amino acid side chain(s) of P.

Preferably, the hydrophobic modification is an acylation and/or addition of hydrophobic moieties,
more preferably an acylation with C8 to C22 fatty acids,
   such as myristoyl (C14), palmitoyl (C16) or stearoyl (C18),
   even more preferably myristoyl (C14),
or the hydrophobic moiety or moieties is selected from cholesterol, cholesterol derivatives, phospholipids, glycolipids, glycerol esters, steroids, ceramids, isoprene derivatives.

The cyclic peptides of the invention can carry more than one hydrophobic modification, such as two, three, four or more, which can be the same or different.

For example, a cyclic peptide of the invention carries one myristoyl group (C14) and one stearoyl (C18) group.

Preferably, the cyclic peptides of the invention carry one or two hydrophobic modification(s).

In one embodiment, a cyclic peptide of the present invention has the general formula Ia

$$\text{cyclo}[(X)_m\text{—P—}(Y)_n] \qquad (Ia)$$

and carries at least one hydrophobic modification at amino acid side chain(s) of X and/or P.

General formula Ia can also be shown as

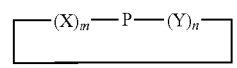

The cyclic peptide with general formula Ia can be obtained via head-to-tail cyclization, such as
   via thiol oxidation (disulfide bridge formation) of two cysteines (C) comprised in the peptide,
      namely a cysteine at the N-terminus and a cysteine at or near the C-terminus (of the peptide sequence before cyclization)

via a lysine (K) at the N-terminus or the N-terminus itself and the C-terminus (of the peptide sequence before cyclization).

For example, a cyclic peptide with general formula Ia can be:

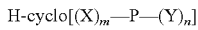

such as

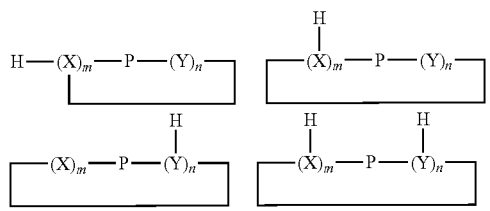

wherein H is the hydrophobic modification, preferably myristoyl (C14).

For example

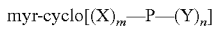

NTCP Targeting

The cyclic peptides of the present invention are preferably suitable to target NTCP (gene name SLC10A1), the sodium taurocholate cotransporter polypeptide.

The human sodium taurocholate cotransporter polypeptide NTCP/SLC10A1 is a HBV preS1-specific receptor which plays a key role in Hepatitis B virus (HBV) and/or Hepatitis D virus (HDV) infection, as it was recently identified by the inventors (see e.g. WO 2014/072526, WO 2014/072524 and WO 2015/014830). Expression of this receptor or of certain non-human counterparts allows to transform cells that were previously unable to specifically bind HBV and/or HDV and/or non-susceptible to HBV and/or HDV infection into cells that are HBV and/or HDV binding-competent and/or susceptible to HBV and/or HDV infection. Cells that became susceptible to HBV and/or HDV infection after differentiation (HepaRG cells) show a significantly increased susceptibility upon expression of NTCP.

NTCP is an integral transmembrane protein, not expressed in HepG2, HuH7, induced in HepaRG cells after DMSO treatment (Kotani et al., 2012) and down-modulated in primary hepatocytes during de-differentiation (Doring et al., 2012).

As used herein, "targeting NTCP" or "NTCP targeting" refers to the specific binding of the cyclic peptides of the present invention to the NTCP receptor on respective liver cells/hepatocytes, preferably within a host (subject or patient) but also in some animals that express a binding competent NTCP although they do not support infection (e.g. mouse, rat, dog).

In one embodiment, the NTCP-mediated transport of bile acids is decreased or blocked by the cyclic peptides of the present invention (in case when NTCP is saturated with cyclic peptide(s).

The HBV/HDV receptor function of NTCP is, however, already blocked, even though NTCP is not saturated with the cyclic peptide(s) indicating different pharmacological doses required for virus inhibition or the inhibition of substrate transport.

Accessory Domain(s)

In one embodiment, a cyclic peptide of the present invention further comprises (accessory) domain(s).

Such accessory domain(s) increase the functionality of the cyclic peptides of the invention. Preferably, said accessory domain(s) provide epitopes that provoke antibody responses with additional neutralizing potential for HBV and HDV.

For example, introduction of the well characterized amino acid sequence motif 19-LDPAFG-24.

Such accessory domain(s) can be part of the cyclic peptide or can be acyclic.

For example, in an embodiment of a cyclic accessory domain, the cyclic peptide contains amino acid residues 8 to 16 of the preS sequence and in addition e.g. amino acid residues 20 to 26 or 20 to 48 of the preS sequence as accessory domain.

In one embodiment of an acyclic accessory domain, the accessory domain is linked/attached to an amino acid side chain of X and/or Y, such as a lysine side chain.

Preferably, the accessory domain is not linked/attached to an amino acid side chain of P.

Preferably, the cyclic peptide of the present invention comprises or consists of an amino acid sequence selected from the group of (wherein P, SEQ ID NO. 1 is underlined and the accessory domain is italic)

Amino Acid Residues 9 to 15

```
                                            (SEQ. ID NO: 2)
            HBVpreS9-15 NPLGFFP
``` and e.g. additional amino acids, such as comprising a N-terminal and a C-terminal cysteine (in the peptide sequence before cyclization)

```
       X = Cys, Y = Cys, m = 1 and n = 1
                                            (SEQ. ID NO: 4)
         Cys-preS9-15-Cys C-NPLGFFP-C
``` such as a C-terminal D-Tyr

```
                                            (SEQ. ID NO: 5)
     Cys-HBVpreS9-15-Cys-D-Tyr C-NPLGFFP-C-y
```

Amino Acid Residues 9 to 16

```
                                            (SEQ. ID NO: 6)
            HBVpreS9-16 NPLGFFPD
``` and e.g. additional amino acids, such as comprising a N-terminal and a C-terminal cysteine (in the peptide sequence before cyclization)

```
      X = Cys, Y = Asp-Cys, m = 1 and n = 2
                                            (SEQ. ID NO: 7)
        Cys-HBVpreS9-16-Cys C-NPLGFFPD-C
``` such as a C-terminal D-Tyr

```
                                            (SEQ. ID NO: 8)
     Cys-HBVpreS9-16-Cys-D-Tyr C-NPLGFFPD-C-y
```

Amino Acid Residues 8 to 16

HBVpreS8-16 PNPLGFFPD (SEQ. ID NO: 9)

and e.g. additional amino acids,
such as comprising a N-terminal and a C-terminal cysteine (in the peptide sequence before cyclization)

X = Cys-Pro, Y = Asp-Cys, m = 2 and n = 2
Cys-HBVpreS8-16-Cys C-PNPLGFFPD-C (SEQ. ID NO: 10)

such as a C-terminal D-Tyr

Cys-HBVpreS8-16-Cys-D-Tyr C-PNPLGFFPD-C-y (SEQ. ID NO: 11)

Amino Acid Residues 9 to 17

HBVpreS9-17 NPLGFFPDH (SEQ. ID NO: 12)

and e.g. additional amino acids,
such as comprising a N-terminal and a C-terminal cysteine (in the peptide sequence before cyclization)

X = Cys, Y = Asp-His-Cys, m = 1 and n = 3
Cys-HBVpreS9-17-Cys C-NPLGFFPDH-C (SEQ. ID NO: 13)

such as a C-terminal D-Tyr

Cys-HBVpreS9-17-Cys-D-Tyr C-NPLGFFPDH-C-y (SEQ. ID NO: 14)

Amino Acid Residues 8 to 17

HBVpreS8-17 PNPLGFFPDH (SEQ. ID NO: 15)

and e.g. additional amino acids,
such as comprising a N-terminal and a C-terminal cysteine (in the peptide sequence before cyclization)

X = Cys-Pro, Y = Asp-His-Cys, m = 2 and n = 3
Cys-HBVpreS8-17-Cys C-PNPLGFFPDH-C (SEQ. ID NO: 16)

such as a C-terminal D-Tyr

Cys-HBVpreS8-17-Cys-D-Tyr C-PNPLGFFPDH-C-y (SEQ. ID NO: 17)

Amino Acid Residues 2 to 21

HBVpreS2-21 GTNLSVPNPLGFFPDHQLDP (SEQ. ID NO: 18)

and e.g. additional amino acids,
such as comprising a N-terminal and a C-terminal cysteine (in the peptide sequence before cyclization)

X = CGTNLSVP, Y = DHQLDPC, m = 8 and n = 7
Cys-HBVpreS2-21-Cys C-GTNLSVPNPLGFFPDHQLDP-C (SEQ. ID NO: 19)

such as a C-terminal D-Tyr

Cys-HBVpreS2-21-Cys-D-Tyr C-GTNLSVPNPLGFFPDHQLDP-C-y (SEQ. ID NO: 20)

Amino Acid Residues 2 to 48 of Genotype C

HBVpreS2-48 GTNLSVPNPLGFFPDHQLDPAFGANSNNPDWDFNPNKD HWPEANQVG (SEQ. ID NO: 21)

and e.g. additional amino acids,
such as comprising a N-terminal and a C-terminal cysteine (in the peptide sequence before cyclization)

X = CGTNLSVP, Y = DHQLDPAFGANSNNPDWDFNPNKDHWPEANQV GC, m = 8 and n = 34
Cys-HBVpreS2-48-Cys C-GTNLSVPNPLGFFPDHQLDPAFGANSNN PDWDFNPNKDHWPEANQVG-C (SEQ. ID NO: 22)

such as a C-terminal D-Tyr

Cys-HBVpreS2-48-Cys-D-Tyr
C-GTNLSVPNPLGFFPDHQLDPAFGANSNNPDWDFNPNKDHWPEANQVG-C-y (SEQ. ID NO: 23)

Amino Acid Residues of Myrcludex B

GTNLSVPNPLGFFPDHQLDPAFGANSNNPDWDFNPNKDHWPEANKVG (SEQ. ID NO: 24)

and e.g. additional amino acids,
such as comprising a N-terminal and a C-terminal cysteine (in the peptide sequence before cyclization)

X = CGTNLSVP, Y = DHQLDPAFGANSNNPDWDFNPNKDHWPEANK VGC, m = 8 and n = 34

Cys-Myrcludex B-Cys
C-GTNLSVPNPLGFFPDHQLDPAFGANSNNPDWDFNPNKDHWPEANKVG-C (SEQ. ID NO: 25)

such as a C-terminal D-Tyr

Cys-Myrcludex B-Cys-D-Tyr
C-GTNLSVPNPLGFFPDHQLDPAFGANSNNPDWDFNPNKDHWPEANKVG-C-y (SEQ. ID NO: 26)

Examples of preferred cyclic peptides of the present invention are:

cyclo[NPLGFFP] (SEQ. ID NO: 2)

cyclo[NPLGFFPD] (SEQ. ID NO: 6)

cyclo[PNPLGFFPD] (SEQ. ID NO: 9)

cyclo[NPLGFFPDH] (SEQ. ID NO: 12)

cyclo[PNPLGFFPDH] (SEQ. ID NO: 15)

cyclo[GTNLSVPNPLGFFPDHQLDP] (SEQ. ID NO: 18)

cyclo[GTNLSVPNPLGFFPDHQLDPAFGANSNNPDWDFNPNKDHWPEANQVG] (SEQ. ID NO: 21)

cyclo[GTNLSVPNPLGFFPDHQLDPAFGANSNNPDWDFNPNKDHWPEANKVG] (SEQ. ID NO: 24)

or

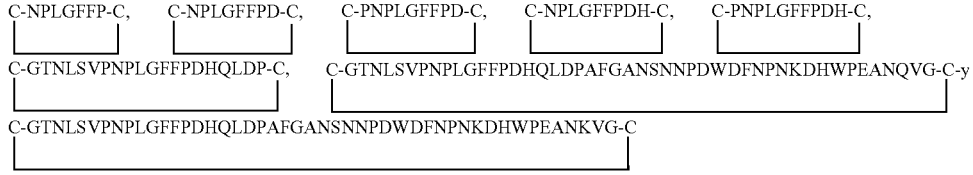

Preferably the above comprise a C-terminal D-amino acid, such as D-tyrosine, e.g.

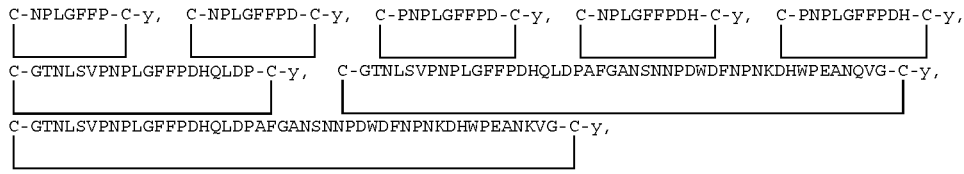

Examples of preferred cyclic peptides of the present invention, with an N-terminal hydrophobic modification (e.g. myristoylation) are:

Myr-cyclo [HBVpreS9-15]
myr-cyclo[NPLGFFP] (SEQ. ID NO: 2)

Myr-cyclo [HBVpreS9-16]
myr-cyclo[NPLGFFPD] (SEQ. ID NO: 6)

Myr-cyclo [HBVpreS8-16]
myr-cyclo[PNPLGFFPD] (SEQ. ID NO: 9)

Myr-cyclo [HBVpreS9-17]
myr-cyclo[NPLGFFPDH] (SEQ. ID NO: 12)

Myr-cyclo [HBVpreS8-17]
myr-cyclo[PNPLGFFPDH] (SEQ. ID NO: 15)

Myr-cyclo-[HBVpreS2-21]
myr-cyclo[GTNLSVPNPLGFFPDHQLDP] (SEQ. ID NO: 18)

Myr-cyclo-[HBVpreS2-48]
myr-cyclo[GTNLSVPNPLGFFPDHQLDPAFGANSNNPDWDFNPNKDHWPEANQVG] (SEQ. ID NO: 21)

Myr-cyclo-[HBVpreS2-48] = cyclic Myrcludex B
myr-cyclo[GTNLSVPNPLGFFPDHQLDPAFGANSNNPDWDFNPNKDHWPEANKVG] (SEQ. ID NO: 24)

In other embodiments, the cyclic peptides comprise P NPLGFXaaP with Xaa=L, i.e. NPLGFLP (SEQ ID NO. 3).

Respective examples of preferred cyclic peptides of the present invention are:

cyclo[NPLGFLP] (SEQ ID NO. 3)

cyclo[NPLGFLPD] (SEQ ID NO. 27)

cyclo[PNPLGFLPD] (SEQ ID NO. 28)

cyclo[NPLGFLPDH] (SEQ ID NO. 29)

cyclo[PNPLGFLPDH] (SEQ ID NO. 30)

cyclo[GTNLSVPNPLGFLPDHQLDP] (SEQ ID NO. 31)

cyclo[GTNLSVPNPLGFLPDHQLDPAFGANSNNPDWDFNPNKDHWPEANQVG] (SEQ ID NO. 32)

```
                                           (SEQ ID NO. 33)
cyclo[GTNLSVPNPLGFLPDHQLDPAFGANSNNPDWDFNPNKDHW

PEANKVG].
```

In one embodiment, a cyclic peptide of the present invention comprises a further moiety or moieties.

Such further moiety or moieties can be
drug(s) or their respective prodrug(s);
tag(s);
label(s),
  such as fluorescent dye(s), radioisotope(s) and contrast agent(s);
recombinant virus(es) or derivative(s) thereof;
carrier or depot(s) for drug(s), prodrug(s) or label(s);
immunogenic epitope(s);
hormones;
inhibitor(s);
toxins.

Such further moiety or moieties are preferably covalently attached, such as via a linker, spacer and/or anchor group(s), e.g. a cleavable linker.

Preferred radioisotopes are $^{131}$I, $^{125}$I, $^{99m}$Tc, $^{18}$F, $^{68}$Ga, $^{111}$In, $^{90}$Y, $^{177}$Lu.

In one embodiment, amino acid residue lysine can be attached/coupled to DOTA[$^{68}$Ga] (i.e. K(DOTA[$^{68}$Ga]).

Preferred fluorescent dyes are Alexa dyes, derivatives of rhodamine and fluorescein, Cy-dyes.

In one embodiment, amino acid residue lysine can be attached/coupled to the fluorescent dye Atto 488 (i.e. K(Atto$_{488}$).

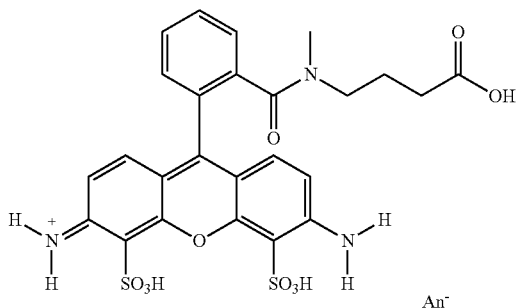

Preferred contrast agents are Gadolinium (Gd) complexes, supramagnetic iron (Fe) complexes and particles, compounds containing atoms of high atomic number, i.e. iodine for computer tomography (CT), microbubbles and carriers such as liposomes that contain these contrast agents.

In one embodiment, the cyclic peptide comprises an inhibitor, such as a capsid inhibitor, preferably covalently attached.

Such inhibitors have been shown to interfere with HBV infection through destabilization HBV genome containing nucleocapsids and therefore interfer with a post-entry step by e.g. disturb intracellular nucleocapsid trafficking and maturation of nucleocapsids (Wang et al., 2015; Cho et al., 2013; Stray et al., 2006)

The cyclic peptide and the capsid inhibitor can act as a combination inhibitor which
(i) addresses and inhibits NTCP, as well as
(ii) interferes with virus replication via targeting the liver by interaction with NTCP and subsequent affecting the nucleocapsid with its second active domain.

The envelope of HBV encloses three proteins termed L (large), M (middle) and S (small). They share the C-terminal S-domain with four transmembrane regions. The M- and L-protein carry additional N-terminal extensions of 55 and, genotype-dependent, 107 or 118 amino acids (preS2- and preS1).

Thus, the expression "preS-derived" peptide of HBV according to the present invention refers to a peptide with an amino acid sequence that corresponds to the N-terminal extensions of the L-protein of HBV, preS1, preferably to a consensus sequence of the species and genotypes A to H as well as of woolly monkey (WMHBV), chimpanzee and gorilla hepatitis B viruses, but it also refers to variants thereof, such as N-terminally and/or C-terminally truncated variants, amino acid substitution variants.

A peptide or amino acid sequence (a) preferably refers to a peptide with an amino acid sequence that corresponds to or is based on the N-terminal extensions of the L-protein of HBV, preS1, preferably of genotypes A to H as well as of woolly monkey (WMHBV), orangutan, chimpanzee and gorilla hepatitis B viruses and the recently described bat hepatitis B virus, but it also refers to variants thereof, preferably C-terminally truncated variants, amino acid substitution variants.

As an indispensible or essential sequence, the amino acid residues being important for the binding of the cyclic peptides of the present invention, as set out in P=SEQ ID NO: 1 (NPLGFXaaP) are present in the peptide/amino acid sequence of the cyclic peptides of the invention.

In particular, the peptides are based on the following sequences (amino acids in single letter code; essential domain or pharmacophore underlined).

Essential Domain/Pharmacopohore (SEQ ID NO: 1):
NPLGFXP (wherein X or Xaa is an arbitrary amino acid, preferably F or L, more preferably F)

```
preS HBV-A (ID: M57663; SEQ ID NO: 34):
MGGWSSKPRKGMGTNLSVPNPLGFFPDHQLDPAFGANSNNPDWDFNPIK

DHWPQANQVGVGAFGPGFTPPHGGVLGWSPQAQGILATVPAMPPPASTN

RQSGRQPTPISPPLRDSHPQA preS HBV-B (ID: D00329, SEQ ID NO: 35)
MGGWSSKPRKGMGTNLSVPNPLGFFPDHQLDPAFKANSENPDWDLNPHK

DNWPDAHKVGVGAFGPGFTPPHGGLLGWSPQAQGILTSVPAAPPPASTN

RQSGRQPTPLSPPLRDTHPQA preS HBV-C (ID: AB048704, SEQ ID NO: 36)
MGGWSSKPRKGMGTNLSVPNPLGFFPDHQLDPAFKANSENPDWDLNPHK

DNWPDAHKVGVGAFGPGFTPPHGGLLGWSPQAQGILTSVPAAPPPASTN

RQSGRQPTPLSPPLRDTHPQA preS HBV-Chimpanzee (ID: AB032432, SEQ ID NO: 37)
MGQNLSTSNPLGFFPEHQLDPAFKANTNNPDWDFNPKKDYWPEANKVGA

GAFGPGFTPPHGGLLGWSPQAQGILTTLPANPPPASTNRQSGRQPTPLS

PPLRDTHPQA preS HBV-D ID: AB048702, SEQ ID NO: 38)
MGQNLSTSNPLGFFPDHQLDPAFRANTNNPDWDFNPNKDTWPDANKVGA

GAFGLGFTPPHGGLLGWSPQAQGFQTLPANPPPASTNRQSGRQPTPLSP

PLRTTHPQA
``` preS HBV-E (ID: X65657, SEQ ID NO: 39)
MGLSWTVPLEWGKNISTT<u>NPLGFFP</u>DHQLDPAFRANTRNPDWDHNPNKD

HWTEANKVGVGAFGPGFTPPHGGLLGWSPQAQGMLKTLPADPPPASTNR

QSGRQPTPITPPLRDTHPQA preS HBV-F (ID: X69798@8, SEQ ID NO: 40)
MGAPLSTTRRGMGQNLSVP<u>NPLGFFP</u>DHQLDPLFRANSSSPDWDFNTNK

DSWPMANKVGVGGYGPGFTPPHGGLLGWSPQAQGVLTTLPADPPPASTN

RRSGRKPTPVSPPLRDTHPQA preS HBV-G (ID: AF160501, SEQ ID NO: 41)
MGLSWTVPLEWGKNLSAS<u>NPLGFLP</u>DHQLDPAFRANTNNPDWDFNPKKD

PWPEANKVGVGAYGPGFTPPHGGLLGWSPQSQGTLTTLPADPPPASTNR

QSGRQPTPISPPLRDSHPQA

HBV Gibbon (ID: AJ131572, SEQ ID NO: 42)
MGQNHSVT<u>NPLGFFP</u>DHQLDPLFRANSNNPDWDFNPNKDTWPEATKVGV

GAFGPGFTPPHGGLLGWSPQAQGILTTLPAAPPPASTNRQSGRKATPIS

PPLRDTHPQA

HBV-H (ID: Q8JMY6, SEQ ID NO: 43)
MGAPLSTARRGMGQNLSVP<u>NPLGFFP</u>DHQLDPLFRANSSSPDWDFNTNKD

NWPMANKVGVGGFGPGFTPPHGGLLGWSPQAQGILTTSPPDPPPASTNRR

SGRKPTPVSPPLRDTHPQA

HBV Orangutan (ID: AF 193864, SEQ ID NO: 44)
MGQNLSVS<u>NPLGFFP</u>EHQLDPLFRANTNNPDWDFNPNKDTWPEATKVGVG

AFGPGFTPPHGGLLGWSPQAQGVTTILPAVPPPASTNRQSGRQPTPISPP

LRDTHPQA

HBV Woolly Monkey (ID: NC 001896, SEQ ID NO: 45)
MGLNQSTF<u>PLGFFP</u>SHQLDPLFKANAGSADWDKPKDPWPQAHDTAVGAFG

PGLVPPHGGLLGWSSQAQGLSVTVPDTPPPPSTNRDKGRKPTPATPPLRD

THPQA

There also exists a HBV preS consensus sequence (for amino acid positions (−11) to 48) (SEQ ID NO: 46):

(-11)-M GGWSS TPRKG MGTNL SVP<u>NP LGFFP</u> DHQLD PAFRA

NSNNP DWDFN PNKDH WPEAN KVG-48

Furthermore, the peptide or amino acid sequences are preferably L-amino acid sequences, but can also comprise D-amino acids or are D-amino acid sequences.

Furthermore, the peptide or amino acid sequences can also comprise unnatural amino acids, which are preferably used for cyclization.

According to the invention, the cyclic peptides of the present invention with general formula I

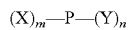

$(X)_m-P-(Y)_n$ comprise or consist of at least the 7 amino acids having the sequence of SEQ ID NO: 1 (P).

Furthermore and discussed above, preferably, m+n is 0 to 42,
and/or m=0 to 8 and/or n=0 to 34, provided that m+n is 0 or at least 1.

A cyclic peptide of the present invention can comprise or consist of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 amino acids.

Synthesis of the Cyclic Peptides

The peptides of this invention can be prepared by a variety of procedures readily known to those skilled in the art, in general by synthetic chemical procedures.

Synthetic chemical procedures include more particularly the solid phase sequential and block synthesis (Erickson & Merrifield, 1976). The solid phase sequential procedure can be performed using established automated methods such as by use of an automated peptide synthesizer. In this procedure an α-amino protected amino acid is bound to a resin support. The resin support employed can be any suitable resin conventionally employed in the art for the solid phase preparation of (poly)peptides, preferably polystyrene which has been copolymerized with polyoxyethylen to provide sites for ester formation with the initially introduced o-amino protected amino acid. This optimized method, applied by the inventors, has been explicitly described (see e.g. Gausepohl et al., 1989). The amino acids are introduced one by one (step-wise). Each synthesis cycle corresponding to the introduction of one amino acid includes a deprotection step, successive washing steps, a coupling step with activation of the amino acid, and subsequent washing steps. Each of these steps is followed by a filtration. The reactive agents for coupling are the classical reactive agents for (poly)peptide synthesis such as dicyclohexylcarbodiimide, hydroxybenzotriazole, benzotriazil-1-yl-oxytris (dimethylamino) phosphonium hexafluorophosphate, and diphenylphosphorylazide. After synthesis of the polypeptide on the resin, the polypeptide is separated from the resin by a treatment with a strong acid such as trifluoroacetic acid in the presence of anisol, ethanedithiol or 2-methylindole. The compound is then purified by the classical techniques of purification, in particular by means of HPLC.

The peptides of the present invention may also be obtained by coupling (poly)peptide fragments that are selectively protected, this coupling being effected e.g. in a solution.

For synthesis of Myrcludex B, see also Schieck et al., 2010.

Peptide Cyclisation Strategies

Generally, covalent peptide cyclisation can be achieved by the formation of any chemical bond. The main strategies followed are cyclisation by the formation of disulfide bonds or amide bonds. The general aspects of peptide cyclization have been comprehensively reviewed by White and Yudin (2011).

For peptide cyclisation, first the linear peptide is synthesized (in most cases by solid-phase peptide synthesis (SPPS)).

As described by White and Yudin (2011) amide bond formation—the head to tail cyclization requires the availability of a carboxylic acid moiety with an appropriate convergent protecting group, i.e. a carbamate linked to an allylic ester (an Alloc group). The cyclisation is achieved either on the solid support or in solution using activation agents such as HBTU. In case of peptides linked by disulfide bonds, the cyclization requires the availability of two thiol groups with an appropriate convergent protecting groups such as Trityl-protecting groups. The cyclisation is achieved by oxidation using agents such as hydrogen peroxide or milder conditions as available by air oxidation.

Pharmaceutical Compositions

As discussed above, the present invention provides a pharmaceutical composition.

The pharmaceutical compositions according to the present invention comprise
(i) at least one cyclic peptide of the present invention,
(ii) optionally, a pharmaceutically acceptable carrier and/or excipient.

The pharmaceutical compositions according to the present invention are very well suited for all the uses and methods described herein.

As outlined above, the present invention provides a vaccine composition comprising at least one cyclic peptide of the present invention and optionally a pharmaceutically acceptable carrier and/or excipient containing/comprising the immunogenic epitope(s).

The vaccine compositions according to the present invention are very well suited for the uses and methods described herein.

A "pharmaceutically acceptable carrier or excipient" refers to any vehicle wherein or with which the pharmaceutical or vaccine compositions according to the invention may be formulated. It includes a saline solution such as phosphate buffer saline. In general, a diluent or carrier is selected on the basis of the mode and route of administration, and standard pharmaceutical practice.

In a preferred embodiment, the pharmaceutical compositions according to the present invention are formulated for oral administration and, thus, comprise suitable pharmaceutically acceptable carrier(s) and/or excipient(s) for oral administration.

Examples for pharmaceutically acceptable carrier(s) and/or excipient(s) are also liposomes.

Medical Applications

As discussed above, the present invention provides the cyclic peptide of the present invention or the pharmaceutical composition of the present invention for use in medicine.

Thus, the cyclic peptide(s) of the present invention or the pharmaceutical composition(s) according to the invention are suitable and, thus, provided for the diagnosis, prevention and/or treatment of diseases.

As discussed above, the present invention provides the cyclic peptide of the present invention or the pharmaceutical composition of the present invention for use in the inhibition of HBV and/or HDV infection.

As discussed above, the present invention provides the cyclic peptide of the present invention or the pharmaceutical composition of the present invention for use in the prevention of a primary HBV and/or HDV infection.

As discussed above, the present invention provides the cyclic peptide of the present invention or the pharmaceutical composition of the present invention for use as HBV and/or HDV entry inhibitors Preferably, HBV infection of any genotype of HBV is inhibited or prevented.

Preferably, the entry inhibition is via targeting of the sodium taurocholate cotransporter polypeptide (NTCP/ SLC10A1), "NTCP targeting".

As discussed above, in one embodiment, the cyclic peptide and the capsid inhibitor can act as a combination inhibitor which
(i) addresses and inhibits NTCP, as well as
(ii) interferes with virus replication via targeting the liver by interaction with NTCP and subsequent affecting the nucleocapsid with its second active domain.

As discussed above, the present invention provides the cyclic peptide of the present invention or the pharmaceutical composition of the present invention for use in the diagnosis, prevention and/or treatment of a liver disease or condition.

In one embodiment, the liver disease or condition is selected from hepatitis, cirrhosis, haemochromatosis, preferably hepatitis caused by hepatitis A, B, C, D, E, F, G and H virus or concomitant hepatitis caused by viruses, In one embodiment, the liver disease or disorder is a disease which involves a liver stadium of a virus or a non-viral pathogen, such as a tropical disease, malaria, schistosomiasis, leishmaniasis, Morbus Wilson.

In one embodiment, the liver disease or disorder is a liver tumor, preferably hepatocellular carcinoma (HCC).

In one embodiment, the liver disease or disorder is a post-transplantation complication after liver transplantation related to bile salt accumulation within the biliary pathway/a post-transplantation-related liver dysfunction.

In one embodiment, the liver disease or condition is related to sodium taurocholate cotransporter polypeptide (NTCP)-mediated transport of compounds into hepatocytes, or necessitates a delivery of a compound, such as a drug or label, to the site or location of the disease or condition.

Preferably, said liver disease or condition is a liver involved metabolic disease selected from
  intrahepatic cholestasis,
  poisoning of the liver (by liver toxins)/hepatotoxicity,
  drug-induced cholestatic liver disease,
  hyperlipidemia,
  posthepatic cholestasis,
  metabolic syndrome,
  non-alcoholic fatty liver disease (NAFLD),
  glycogen storage diseases, Preferably, the compounds which are transported into hepatocytes via NTCP are preferably bile acids, steroids, conjugated and non-conjugated thyroid hormones, liver toxins, compounds that are covalently bound to taurocholate, bromosulphophthalein, drugs.

The inventors have identified and described the sodium taurocholate cotransporter polypeptide (NTCP) as target and for use in the prevention and/or treatment of certain liver diseases or conditions, such as liver diseases or conditions that are related to NTCP-mediated transport of compounds (such as bile acids etc.) into hepatocytes, preferably liver involved metabolic diseases (e.g. intrahepatic cholestasis, poisoning of the liver (by liver toxins)/hepatotoxicity, drug-induced cholestatic liver disease, hyperlipidemia, etc.) and cardiovascular diseases. See WO 2014/072524 and PCT/ EP2014/066262, which are enclosed herewith in their entirety.

A "liver involved metabolic disease" when used herein refers to metabolic disorders including visceral obesity, diabetes mellitus and dyslipidemia which are influenced by the liver metabolism of lipids and bile acids.

In general, "cholestasis" is a condition where bile constituents cannot be secreted from hepatocytes into the biliary tree or where bile cannot flow from the liver to the duodenum, resulting in hepatocyte bile acid accumulation within hepatocytes.

"Cholestasis" or "intrahepatic cholestasis" when used herein refers to intrahepatic toxic effects of hepatocyte bile acid accumulation related to an insufficient expression and/ or activity of bile salt pumps (like BSEP or MRP) in the canalicular membrane.

"Posthepatic cholestasis" when used herein refers to a cholestatic liver disease due to obstruction of the large bile ducts.

"Poisoning of the liver" or "hepatotoxicity" or "toxic liver disease" when used herein refer to toxic effects of drugs independent of bile acid accumulation. These drugs penetrate the hepatocytes via the NTCP-mediated transport and cause several direct toxic effects, by damaging the mitochondria or by activating enzymes in the cytochrome P-450 system leading to oxidative stress.

"Drug-induced cholestatic liver disease" when used herein refers to inhibition of the export of bile acids from hepatocytes due to drug effects on bile salt export pump (BSEP). Drug-induced cholestasis may be caused by several drugs which inhibit BSEP, such as rifampicin, cyclosporine A, rifamycin SV, bosentan, troglitazone, erythromycin estolate, and glibenclamide (Fattinger et al., 2001; Funk et al., 2001; Funk et al., 2001; Stieger et al., 2000; Dawson et al., 2012; Morgan et al., 2010; Ogimura et al., 2011). BSEP is a member of the ATP-binding cassette (ABC) family of transporters (BSEP is also identified as ABCB11) and it is involved in the process of exporting bile acids out of hepatocytes, thus reducing their toxicity to these cells. The above mentioned drugs cause the toxic effects of excess bile acid accumulation because the excretion of bile acid via BSEP is disabled. Inhibition of NTCP-mediated bile acid uptake via the lipopeptide-based compound (such as MyrB) and NTCP counterbalances BSEP inhibition, and thereby prevents hepatotoxicity or is suitable for treatment and/or diagnosis.

"Hyperlipidemia" (or hyperlipoproteinemia, or hyperlipidemia) involves abnormally elevated levels of any or all lipids and/or lipoproteins in the blood.

Hyperlipidemias are divided in primary and secondary subtypes. Primary hyperlipidemia is usually due to genetic causes (such as a mutation in a receptor protein), while secondary hyperlipidemia arises due to other underlying causes such as diabetes. Lipid and lipoprotein abnormalities are common in the general population, and are regarded as a modifiable risk factor for cardiovascular disease due to their influence on atherosclerosis.

"Hypercholesterolemia" (or hypercholesterolaemia) is the presence of high levels of cholesterol in the blood. It is a form of "hyperlipidemia".

"Hyperlipidemia" when used herein preferably refers to hypercholesterolemia which includes elevated LDL cholesterol, reduced HDL cholesterol, elevated triglycerides, clogged arteries leading to high blood pressure, cardiovascular disease (CVD), heart attacks and strokes.

"Metabolic syndrome" refers to a disorder of energy utilization and storage, diagnosed by a co-occurrence of three out of five of the following medical conditions: abdominal (central) obesity, elevated blood pressure, elevated fasting plasma glucose, high serum triglycerides, and low high-density cholesterol (HDL) levels. Metabolic syndrome increases the risk of developing cardiovascular disease, particularly heart failure, and diabetes. Metabolic syndrome is also known as metabolic syndrome X, cardiometabolic syndrome, syndrome X, insulin resistance syndrome, Reaven's syndrome, and CHAOS.

"Non-alcoholic fatty liver disease" (NAFLD) refers to one cause of a fatty liver, occurring when fat is deposited (steatosis) in the liver not due to excessive alcohol use. It is related to insulin resistance and the metabolic syndrome. Non-alcoholic steatohepatitis (NASH) is the most extreme form of NAFLD, and is regarded as a major cause of cirrhosis of the liver of unknown cause.

Preferably, the NTCP-mediated transport is decreased or blocked by the cyclic peptides of the present invention.

As discussed above, in one embodiment, the cyclic peptide and the capsid inhibitor can act as a combination inhibitor which (i) addresses and inhibits NTCP, as well as
(ii) interferes with virus replication via targeting the liver by interaction with NTCP and subsequent affecting the nucleocapsid with its second active domain.

As discussed above, the present invention provides the cyclic peptide of the present invention or the pharmaceutical composition of the present invention for use in the diagnosis, prevention and/or treatment of a cardiovascular disease (CVD).

Preferably the cardiovascular disease comprises the control or modification of the cholesterol level or cholesterol uptake,
wherein the cholesterol level or uptake is preferably controlled or modified by decreasing or blocking the NCTP-mediated bile salt transport (by the cyclic peptide).

The cholesterol level or uptake is controlled or modified by decreasing or blocking the NCTP-mediated bile salt transport by the cyclic peptide of the present invention.

Said uses comprises the control or modification of the cholesterol level or cholesterol uptake, wherein the cholesterol level or uptake is controlled or modified by decreasing or blocking the NCTP-mediated bile salt transport by the cyclic peptide of the present invention.

Cardiovascular diseases (CVD) are the major cause of morbidity and death in the western world. High levels of cholesterol have been associated with CVD as one of the risk factors. Of particular importance clinically is the abnormal deposition of cholesterol and cholesterol-rich lipoproteins in the coronary arteries. Such deposition, eventually leading to atherosclerosis, is the leading contributory factor in diseases of the coronary arteries. In this case the management of CVD is critical dependent on lipid-lowering therapies. Different classes of drugs are available for this purpose, such as statins, cholesterol absorption inhibitors, bile acid resins, fibrates and nicotinic acid that act by reducing the levels of cholesterol by distinct pathways (Schmitz & Langmann, 2006). These drugs have several side effects and depend on the relative levels of the metabolizing enzymes and transporters that act on cardiovascular drugs.

The main control of cholesterol metabolism is caused by bile acid as an important regulator of cholesterol homeostasis. The levels of bile acid and cholesterol are linked by the regulation of cholesterol metabolism and absorption. The synthesis of the bile acids is the major pathway of cholesterol catabolism in mammals, because the end products of cholesterol utilization are the bile acids. The major pathway for the synthesis of the bile acids is initiated via hydroxylation of cholesterol at the 7 position via the action of cholesterol 7α-hydroxylase (CYP7A1).

That means that the synthesis of bile acids is one of the predominant mechanisms for the excretion of excess cholesterol. Under physiological conditions this regulation is insufficient to compensate for an excess intake of cholesterol. However, if bile acid uptake into hepatocytes is blocked, the excretion of cholesterol in the form of bile acids will be sufficient to compensate for an excess dietary intake of cholesterol. Blocking bile acid uptake via the lipopeptide-based compound according to the invention and NTCP leads to intracellular deficiency of bile acid which is compensated by increased cholesterol metabolism and absorption.

Thus, according to the invention, the cyclic peptides of the present invention are suitable for lipid-lowering therapies to prevent CVD.

Route of Administration

Preferably, the route of administration of cyclic peptides or pharmaceutical compositions of the present invention is selected from oral, subcutaneous, intravenous, nasal, intramuscular, transdermal, inhalative, by suppository.

A preferred route of administration or application is orally.

A preferred embodiment for nasal administration or application is a nasal spray.

Therapeutically Effective Amount

The cyclic peptides or the pharmaceutical compositions of the invention are provided such that they comprise a therapeutically effective amount of said cyclic peptide(s) or of said pharmaceutical composition(s).

A "therapeutically effective amount" of a cyclic peptide or a pharmaceutical composition of this invention refers to the amount that is sufficient to inhibit NTCP receptor function.

Furthermore, said "therapeutically effective amount" depends on the respective application and desired outcome of inhibition, treatment or vaccination.

Different therapeutically effective amounts are necessary for
(i) antiviral use or entry inhibition (such as 0.01 to 0.5 mg per patient, preferably 0.1 to 1 mg/patient)
compared to
(ii) uses which require a saturation of NTCP, such as for inhibition of NTCP-mediated transport of e.g. bile acids, drugs etc. (such as 1 mg per patient or 1-2 mg/patient).

In one embodiment, said "therapeutically effective amount" of a cyclic peptide or a pharmaceutical composition of this invention refers to the amount that is sufficient to inhibit a HBV and/or HDV infection; prevent a primary HBV and/or HDV infection; treat hepatitis B and/or D and/or vaccinate and/or inhibit entry of HBV and/or HDV in vivo.

A preferred therapeutically effective amount is in the range of 10 µg to 1 mg per kg body weight, preferably 10 µg to 100 µg.

Preferably, the therapeutically effective amount is in the range of from about 0.01 mg to about 50 mg per patient and per day, preferably from about 1 mg to about 20 mg per patient per day or is applied to a patient in a dose ranging from 100 nmol per kg to 2 µmol per kg per day/or is applied to a patient in a dose ranging from 10 pmol per kg to 20 µmol per kg body weight.

In case of an $IC_{50}$ value of the cyclic peptide used of about 10 nM, a preferred therapeutically effective amount is about 100 µg per kg body weight or in the range of 1 to 5 mg per patient. The preferred therapeutically effective amount in the range of 1 to 5 mg per patient can be administered once a day or in other embodiments only once every 2-3 days.

The skilled artisan will be able to determine suitable therapeutically effective amounts.

Methods of Diagnosis, Prevention and/or Treatment of Diseases

As discussed above, the present invention provides a method for the inhibition of HBV and/or HDV infection and/or the prevention of a primary HBV and/or HDV infection.

Said method comprises the administration of a therapeutically effective amount of a cyclic peptide of the present invention or a pharmaceutical composition of the present invention.
wherein preferably HBV infection of any genotype of HBV is inhibited or prevented.

As discussed above, the present invention provides a method for the diagnosis, prevention and/or treatment of a liver disease or condition.

Said method comprises the administration of a therapeutically effective amount of a cyclic peptide of the present invention or a pharmaceutical composition of the present invention.

In one embodiment, the liver disease or condition is selected from hepatitis, cirrhosis, haemochromatosis, preferably hepatitis caused by hepatitis A, B, C, D, E, F, G and H virus or concomitant hepatitis caused by viruses.

In one embodiment, the liver disease or disorder is a disease which involves a liver stadium of a virus or a non-viral pathogen, such as a tropical disease, malaria, schistosomiasis, leishmaniasis, Morbus Wilson.

In one embodiment, the liver disease or disorder is a liver tumor, preferably hepatocellular carcinoma (HCC).

In one embodiment, the liver disease or disorder is a post-transplantation complication after liver transplantation related to bile salt accumulation within the biliary pathway.

In one embodiment, the liver disease or condition is related to sodium taurocholate cotransporter polypeptide (NTCP)-mediated transport of compounds into hepatocytes, or necessitates a delivery of a compound, such as a drug or label, to the site or location of the disease or condition, and preferably is a liver involved metabolic disease selected from
  intrahepatic cholestasis,
  poisoning of the liver (by liver toxins)/hepatotoxicity,
  drug-induced cholestatic liver disease,
  hyperlipidemia,
  posthepatic cholestasis,
  metabolic syndrome,
  non-alcoholic fatty liver disease (NAFLD),
  glycogen storage diseases,
and wherein the compounds which are transported into hepatocytes via NTCP are preferably bile acids, steroids, conjugated and non-conjugated thyroid hormones, liver toxins, compounds that are covalently bound to taurocholate, bromosulphophthalein, drugs.

As discussed above, in one embodiment, the cyclic peptide and the capsid inhibitor can act as a combination inhibitor which
(i) addresses and inhibits NTCP, as well as
(ii) interferes with virus replication via targeting the liver by interaction with NTCP and subsequent affecting the nucleocapsid with its second active domain.

As discussed above, the present invention provides a method for the diagnosis, prevention and/or treatment of a cardiovascular disease (CVD).

Said method comprises the administration of a therapeutically effective amount of a cyclic peptide of the present invention or a pharmaceutical composition of the present invention.

Said method preferably comprises the control or modification of the cholesterol level or cholesterol uptake, wherein the cholesterol level or uptake is preferably controlled or modified by decreasing or blocking the NCTP-mediated bile salt transport (by the cyclic peptide).

In the methods of the present invention, and as discussed above, the "therapeutically effective amount" depends on the respective application and desired outcome of inhibition, treatment or vaccination.

Different therapeutically effective amounts are necessary for
(i) antiviral use or entry inhibition (such as 0.01 to 0.5 mg per patient, preferably 0.1 to 1 mg/patient)
compared to
(ii) uses which require a saturation of NTCP (such as 1 mg per patient or 1-2 mg/patient).

In one embodiment, and as discussed above, the therapeutically effective amount is preferably in the range of from about 0.01 mg to about 50 mg per patient, preferably from about 1 mg to about 20 mg per patient, or wherein the cyclic peptide is preferably applied to a patient in a dose ranging from 10 pmol per kg to 20 µmol per kg body weight.

In the methods of the present invention, and as discussed above, the route of administration is preferably selected from oral, subcutaneous, intravenous, nasal, intramuscular, transdermal, inhalative, by suppository.

The following examples and drawings illustrate the present invention without, however, limiting the same thereto.

A, The sequence and structure of the covalently bridged cyclic derivative of Myrcludex B (Myr-2-48 Cyc).

B, The inhibitory activity of Myr-2-48 Cyc is comparable to other Myrcludex B derivatives, such as a linear Myrcludex B derivative with myristoyl group within the peptide sequence (2-Myr-48) and a linear preS-derives peptide 2-21 with a C-terminal myristoyl group (2-21-Myr).

Figure 1:
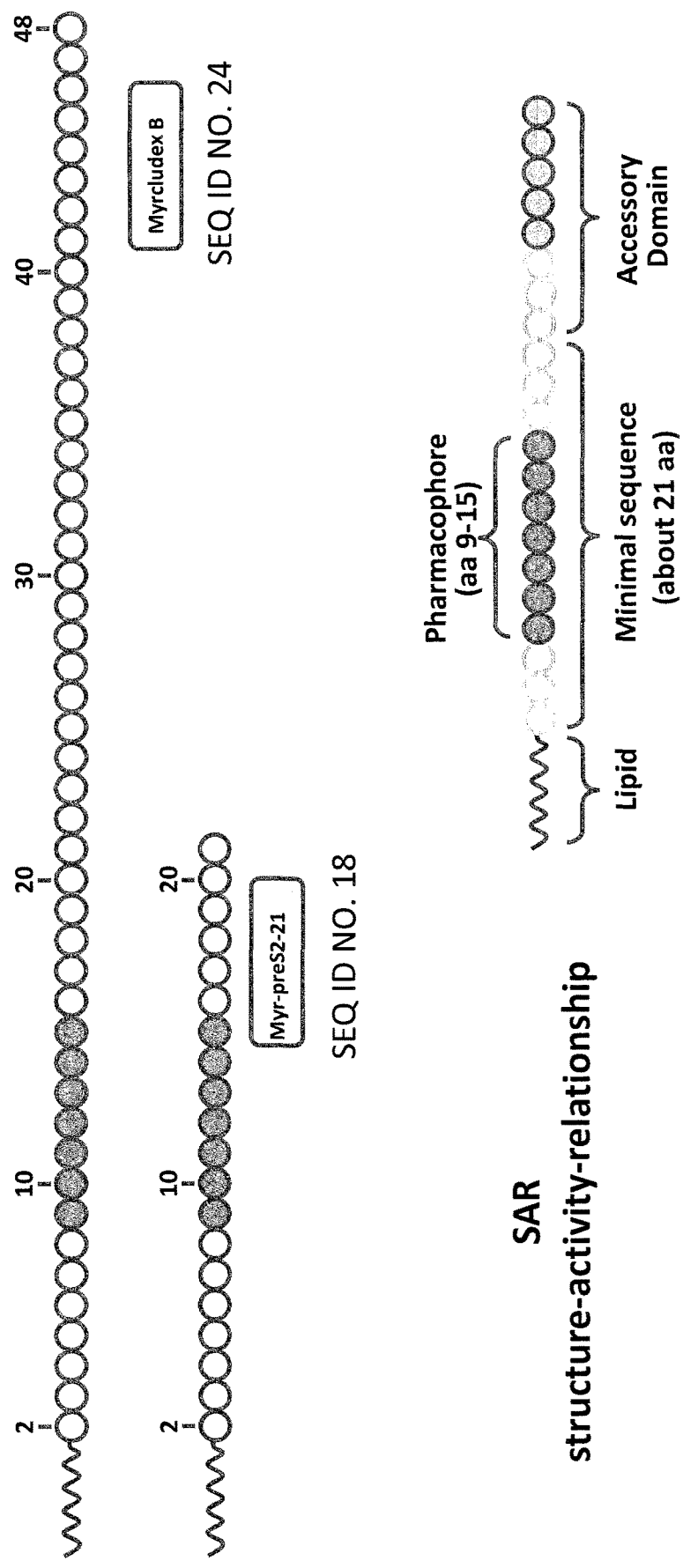
FIG. 1 Myrcludex B and derivatives
Figure 2:
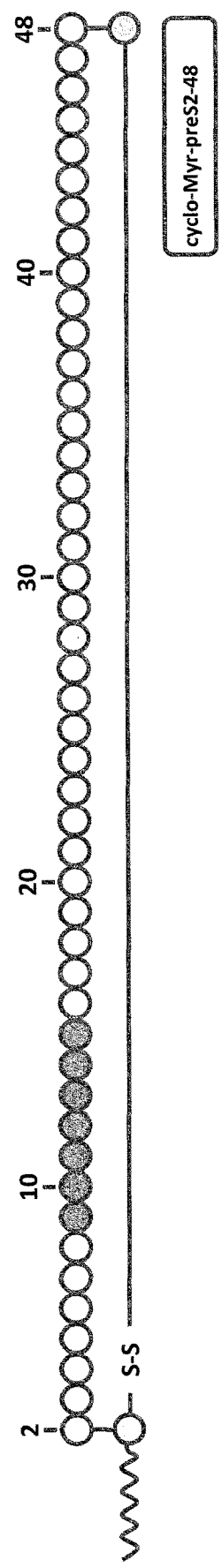
FIG. 2 A covalently bridged cyclic derivative of Myrcludex B shows inhibitory potential.
Figure 2:
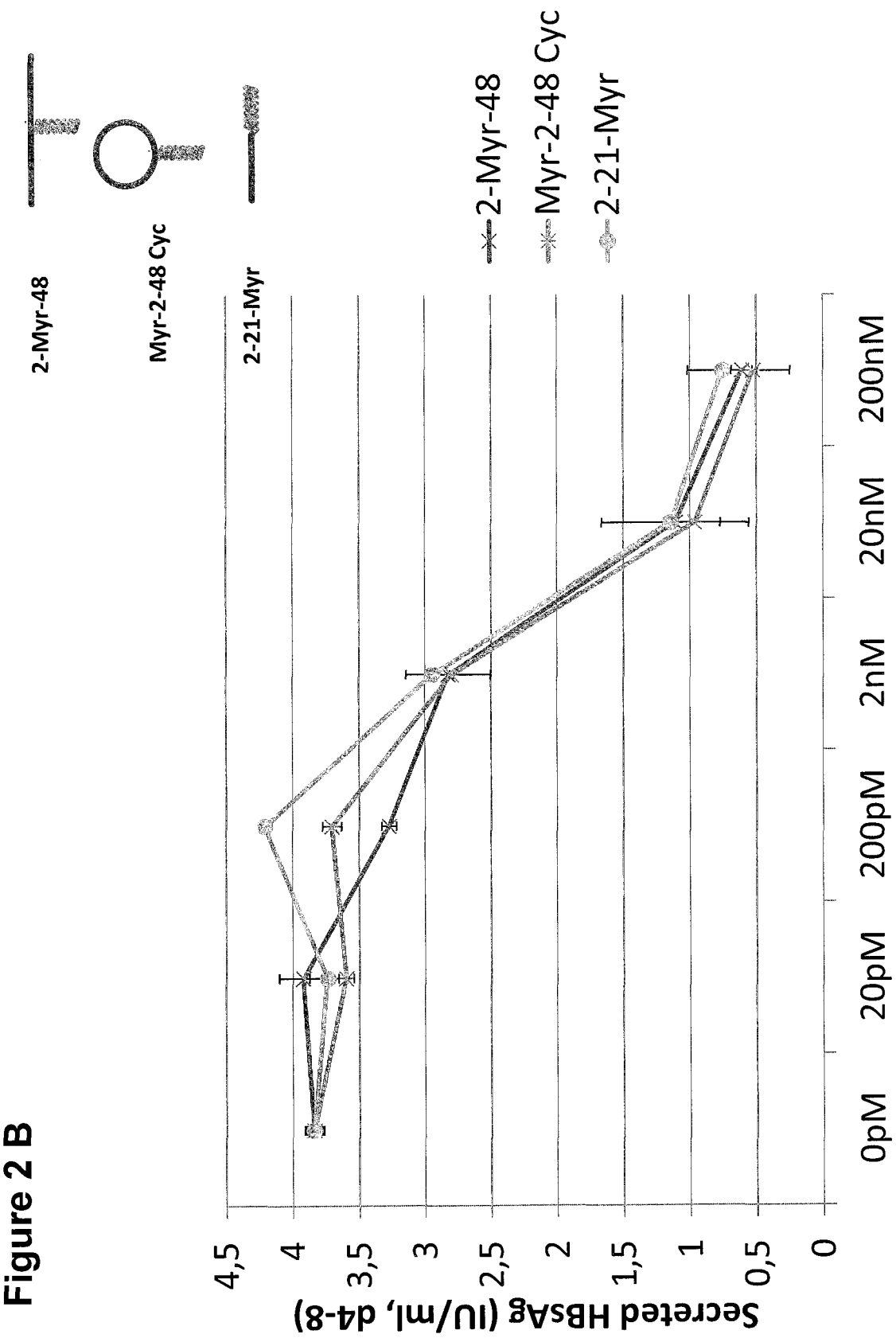
Figure 3:
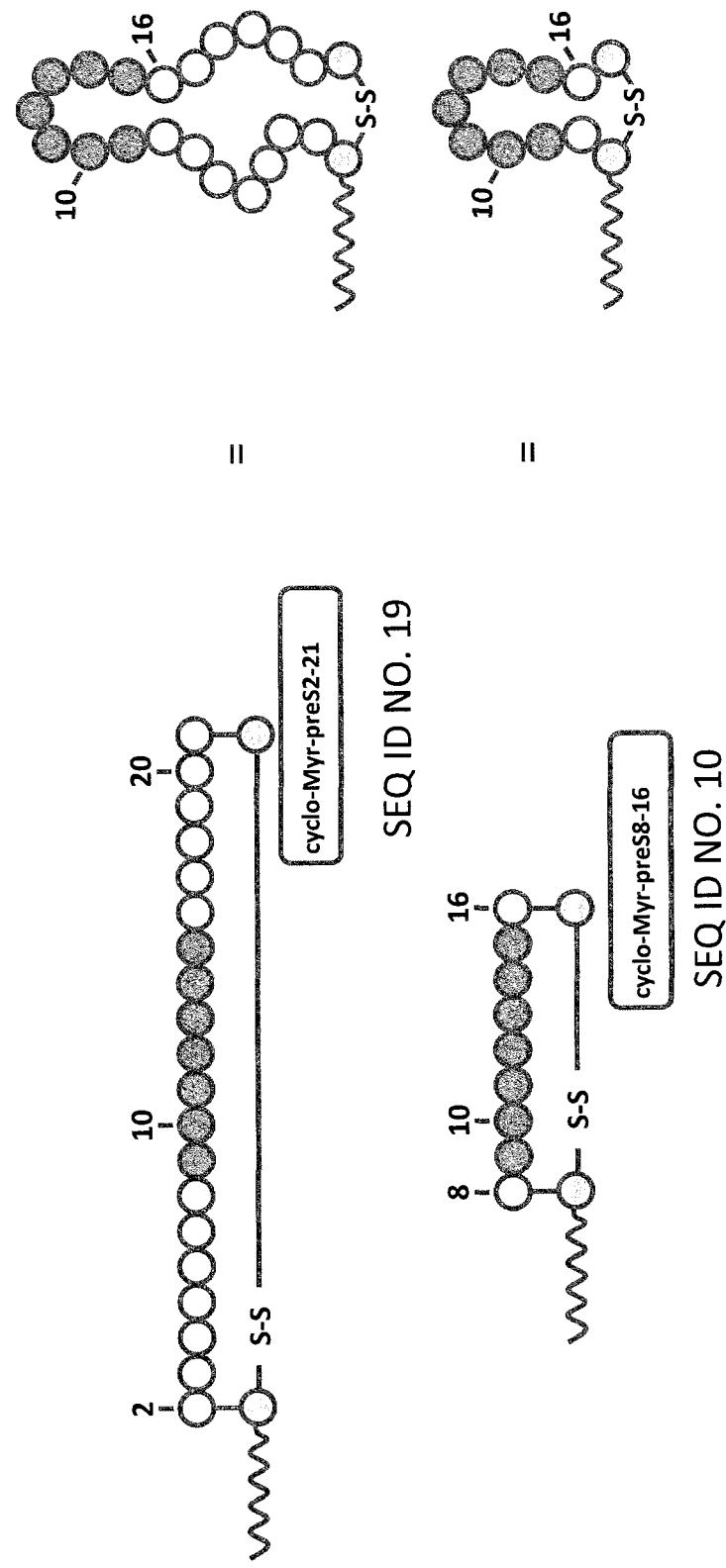

FIG. 3 Further cyclic Myrcludex B derivates

Figure 4:
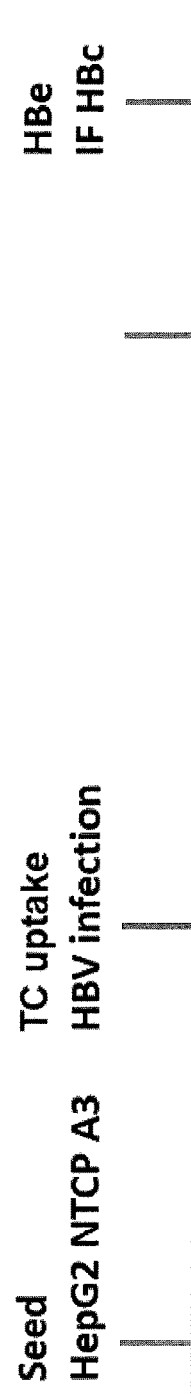

FIG. 4 Further cyclic Myrcludex B derivates

A, Overview of synthesized cysteine cyclized peptides and control peptides

B, Experimental setup for testing of peptides:

HepG2 NTCP cells were seeded in 24 well plates. When cells reached 60-70% confluency, they were subjected to HBV infection or TC uptake assay. Cell supernatant was collected from day 5 to 7 for HBeAg measurement and cells were fixed with 4% PFA at day 7 for immunofluorescence with an anti-HBc antibody.

Figure 5:
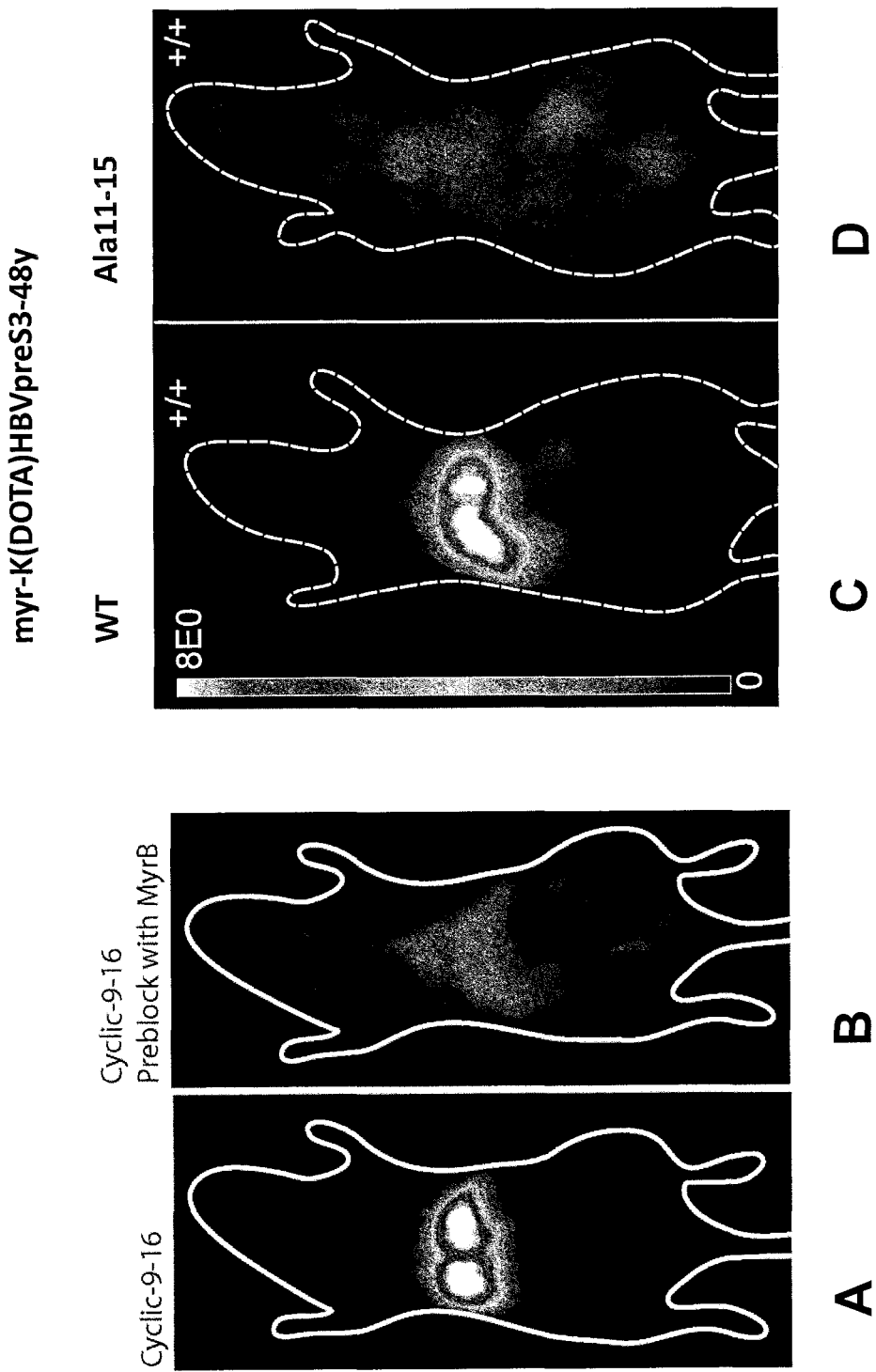

FIG. 5 Coronary PET images 40-60 minutes post injection of $^{68}$Gallium labeled peptides.

A, myr-CNPLGFFPDCK(DOTA[$^{68}$Ga])

B, Liver blocked with cold Myrcludex B 1 µg/g bodyweight 30 minutes prior to injection with myr-CNPLGFFPDCK(DOTA[$^{68}$Ga])

C, Myr-K(DOTA[$^{68}$Ga])HBVpres3-48y (WT peptide)

D, Myr-K(DOTA[$^{68}$Ga])HBVpres3-48y Ala11-15 (Binding incompetent control peptide) See also Slijepcevic et al., 2015.

Figure 6:
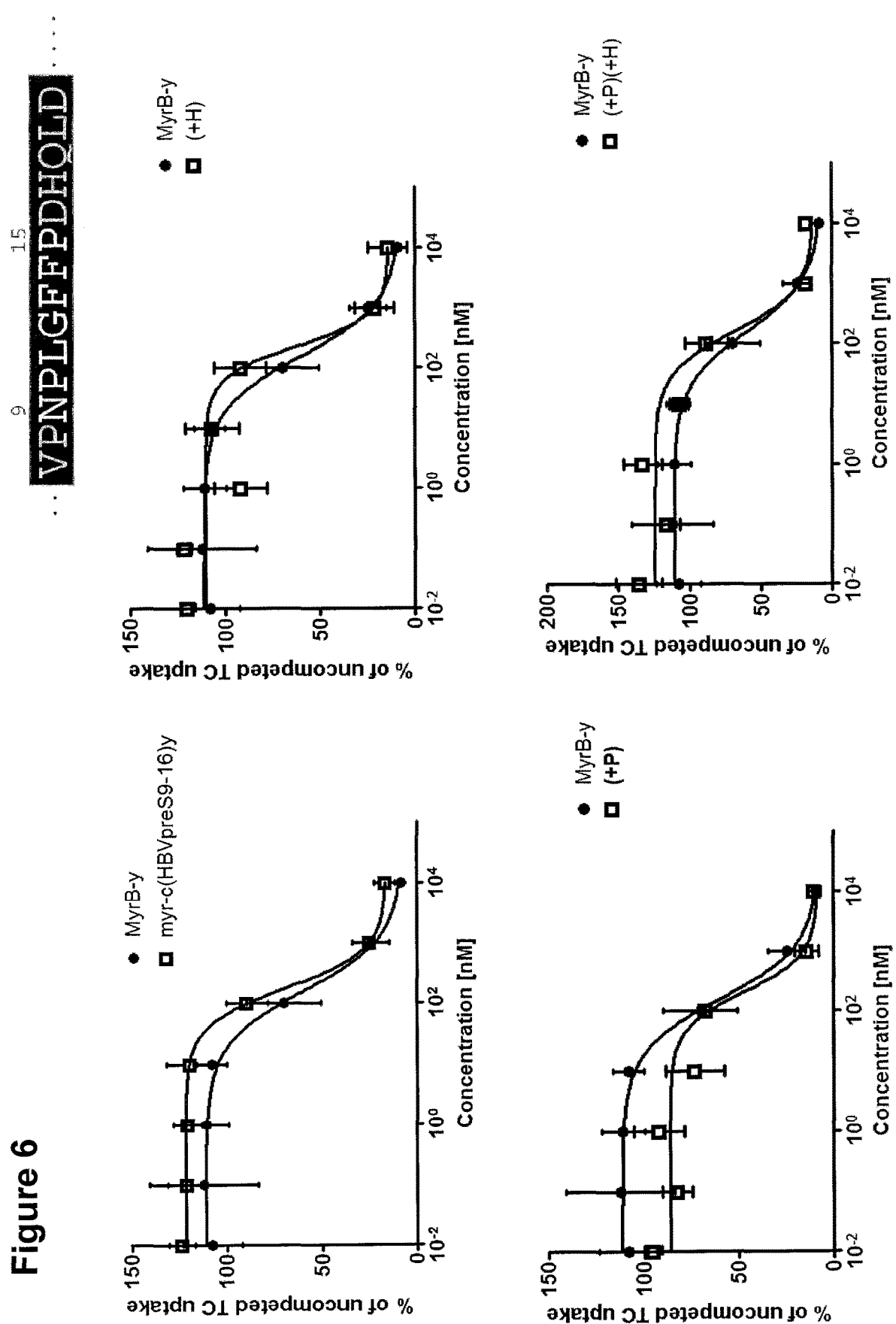
Figure 7:
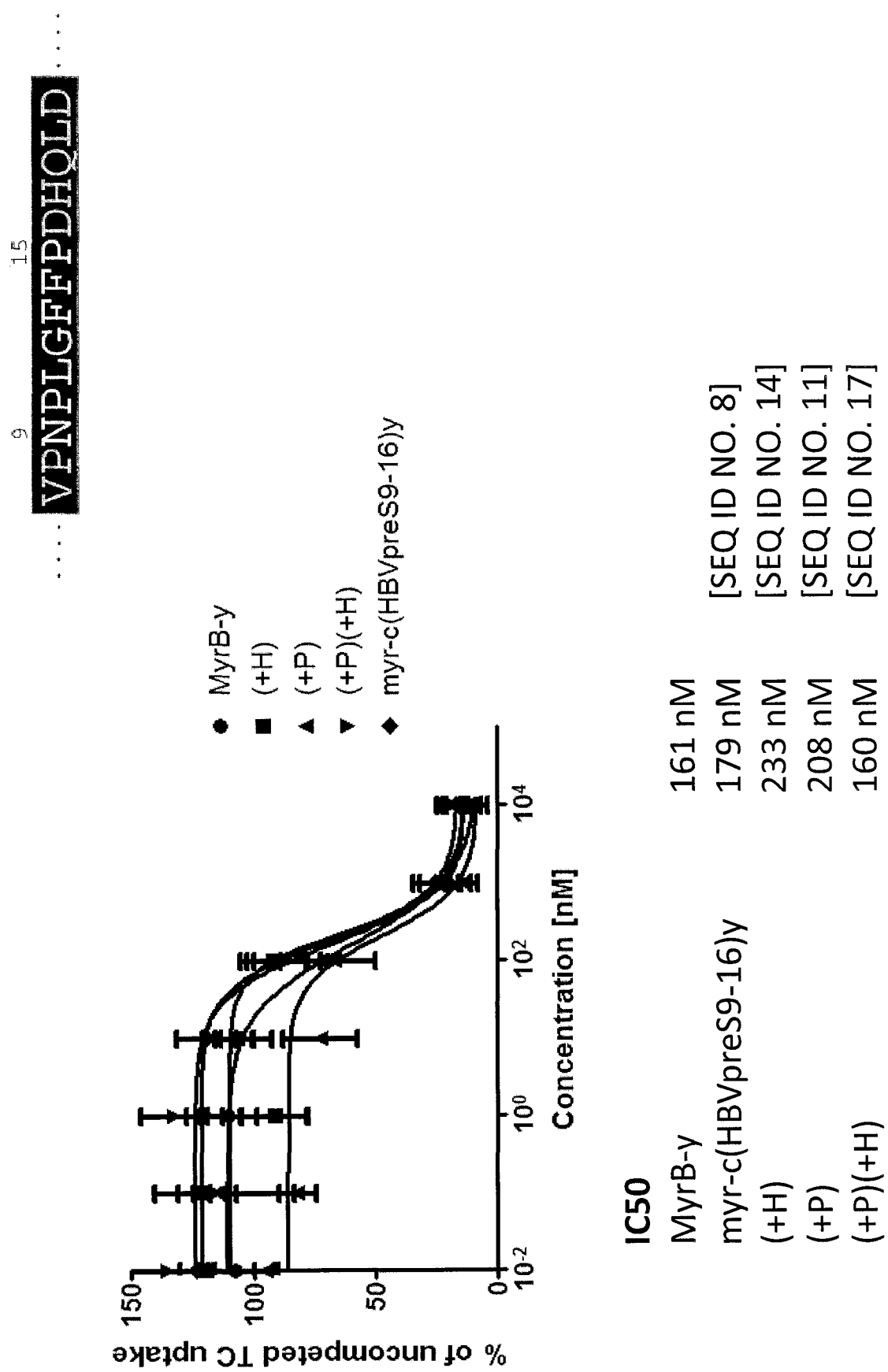
Figure 8:
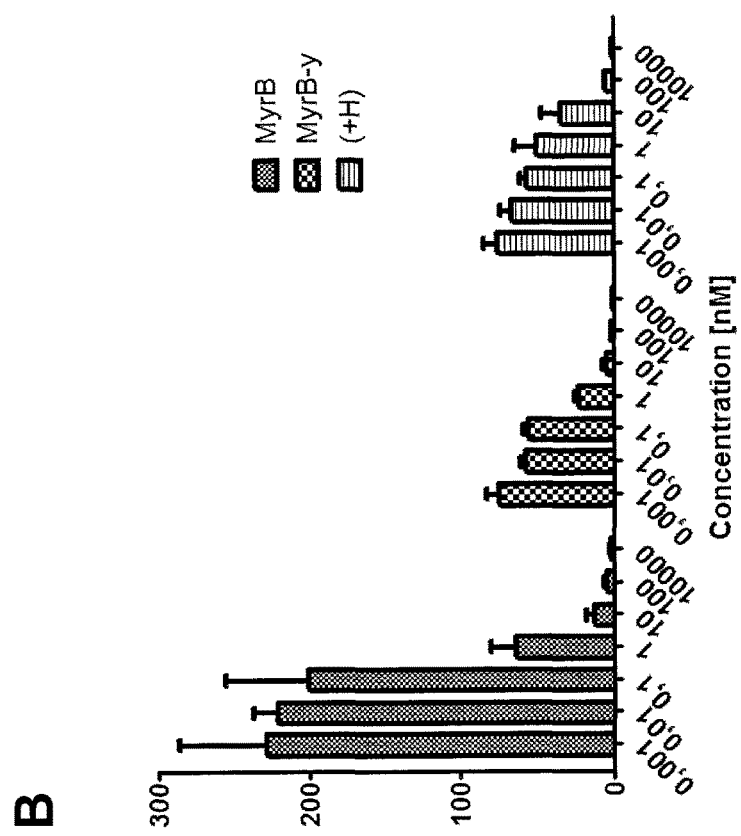
Figure 8:
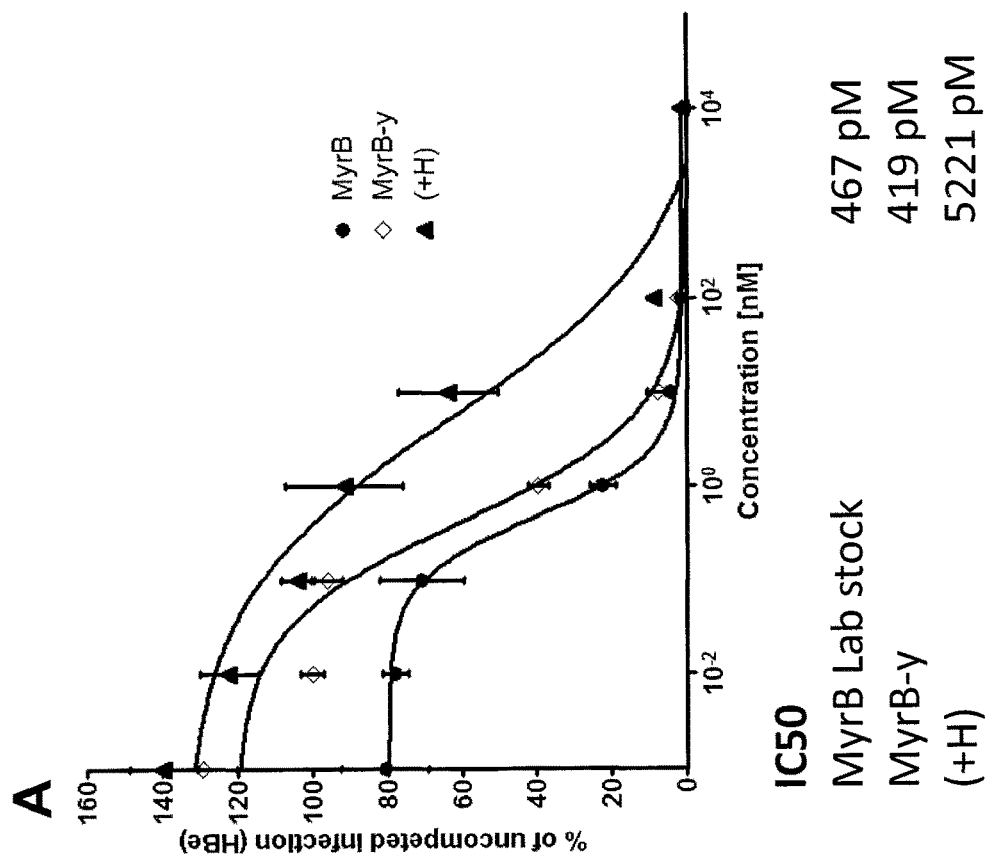

FIG. 6 $^{3}$H-Taurocholate uptake in HepG3 NTCP cells comparison of different cyclic peptides with Myrcludex B FIG. 7 $^{3}$H-Taurocholate uptake in HepG3 NTCP cells: IC 50 values and curves of different cyclic peptides with Myrcludex B FIG. 8 HBV infection inhibition assay on HepG2 NTCP cells.

with Myrcludex B (GMP grade), Myrcludex B-y (self-made) and (+H) cyclic peptide.

A, IC 50 curves and values.

B, Absolute values of HBeAg measurement of supernatants diluted 1:2

EXAMPLES

Example 1 Materials & Methods

Abbreviations

COMU (1-Cyano-2-ethoxy-2-oxoethylidenaminooxy)dimethylamino-morpholino-carbenium-hexafluorophosphate DCM Dichloromethane
DIPEA N,N-diisopropylethylamine
DMF Dimethylformamide
DOTA 1,4,7,10-tetraazacyclododecane-1,4,7,10-tetraacetic acid
Fmoc Fluorenylmethyloxycarbonyl chloride
Ga Gallium
HATU 1-[Bis(dimethylamino)methylene]-1H-1,2,3-triazolo[4,5-b]pyridinium 3-oxid hexafluorophosphate
HBeAg Hepatitis B Virus Early Antigen
HBcAg Hepatitis B Core Antigen
HBTU 2-(1H-benzotriazol-1-yl)-1,1,3,3-tetramethyluronium hexafluorophosphate
HBV Hepatitis B Virus
HPLC High performance liquid chromatography
LC/MS Liquid chromatography-mass spectrometry
NHS N-Hydroxysuccinimide
NMP N-Methyl-2-pyrrolidone
NTCP Sodium taurocholate cotransporting polypeptide
PBS Phosphate buffered saline
PET Positron emission tomography
PFA Paraformaldehyde
TC Taurocholate
TFA Trifluoro acetic acid
TIS Triisopropylsilane 1. Peptide Synthesis 1.1 Disulfide Bridge Peptide Solid Phase Peptide Synthesis Peptides were synthesized on solid phase (Tentagel R RAM resin, capacity 0.22 mmol/g, Rapp Polymere, Tibingen, Germany) using Fmoc/tBu chemistry in peptide synthesizer (Applied Biosystems 443A, Foster City, Calif., USA). Before beginning peptide synthesis the resin (0.05 mmol) was preswollen in DCM. Fmoc-protected amino acids were used in a 10-fold excess (0.5 mmol) and activated with HBTU/DIPEA in NMP.

See also Schieck et al., 2010.

Myristoylation

Peptide on the solid support was swollen in DCM and washed with NMP. Myristic acid (4 eq.) and HATU or COMU (4 eq.) were dissolved in NMP and 10 eq. DIPEA were added. The mixture was added to the resin and was incubated for 30 min. Afterwards the resin was washed three times with NMP, three times with DCM and dried.

Deprotection and Cleavage from Resin

The peptide was cleaved and deprotected with TFA/TIS/H$_2$O (95:2.5:5:2.5). The deprotected peptide was precipitated with diethyl ether, pelleted by centrifugation (3000 rpm, 5 min) and washed twice with fresh diethyl ether. The peptide was dried.

MyrB:

[SEQ ID NO. 24]
Myr-GTNLSVP<u>NPLGFFPD</u>HQLDPAFGANSNNPDWDFNPNKDHWPEANK
VG-amide Disulfide Bridge Formation 5 mg of raw peptide were dissolved in 5 ml 80% acetic acid. 1 mg of iodine in glacial acetic acid was slowly dropped into the peptide solution. 10 µl of saturated ascorbic acid solution were added. The solvent was evaporated and the peptide redissolved in 1:1 acetonitril:H$_2$O and purified with preparative HPLC. The success of the reaction was confirmed by LC/MS.

Coupling of Fluorescent Dye/Compounds

Peptides were dissolved in DMF and reacted with NHS-ester-activated compounds (2 eq.) and DIPEA (10 eq.). The reaction was controlled with HPLC.

1.2 Aminoproline-Peptide 200 mg (0.32 mmol) 2-Chlorotrityl chloride resin was charged with 41 mg (0.1 mmol) Fmoc-Glu(OAll)-OH and 52 mg (68 µL; 0.4 mmol) DIPEA in 2 mL Dichloromethane. After capping with methanol the resin was subjected to automated peptide synthesis (ABI 433A). 109 mg (0.25 mmol) Fmoc-L-Pro(4-NH-Alloc)-OH (2S,4S) were coupled at the desired amino acid position by COMU-activation. Solid phase cyclization was achieved by 110 mg (86 mL; 0.4 mmol) DPPA and 77 mg (102 µL; 0.6 mmol) in 2 mL NMP after linear assembly as well as catalytic allyl-deprotection with 5 mg tetrakis(triphenylphosphine)palladium(0) and 30 mg borane dimethylamine complex. The cyclic peptide was cleaved and deprotected by 95:2.5:2.5 TFA/water/TIS and purified by HPLC; occasionally a portion of the raw peptide was modified with DOTA or fluorescent dye active esters prior to purification 2. $^{68}$Ga-Labeling and PET Imaging Ca. 1 mL of [$^{68}$Ga]Ga$^{3+}$ eluate (ca. 600-800 MBq) was added to a mixture of 20 µL of a 1 mM solution of compound xy in DMSO and 10 µL of saturated solution of ascorbic acid in water. The pH of the resulting mixture was adjusted to 3.5-4.0 by careful addition of a 2.5 M sodium acetate solution in water. Complexation was achieved by heating to over 95° C. for 5-10 minutes under constant stirring. The product was isolated by solid phase extraction with ethanol followed by evaporation. The residue was taken up in 1% bovine serum albumin solution and an appropriate amount (ca. 20-50 MBq) was used for the individual experiment in a volume not exceeding 100 µl. Mice were anesthetized with 1% sevoflurane (Abbott, Wiesbaden, Germany) and images were recorded using an Inveon small animal positron emission tomographic (PET) scanner (Siemens, Knoxville, Tenn.) up to 60 minutes postinjection.

3. $^{3}$H-Taurocholate Uptake Assay

HepG2 NTCP cells seeded in a 24 well format were preincubated with the indicated peptide for 30 min at 37° C. in culture medium. 150 µM taurocholate (containing 450 cpm/fmol $^{3}$H taurocholate) were added to each well and the cells were incubated an additional 15 minutes at 37° C. Uptake was stopped by removal of the cell culture medium and addition of ice cold PBS. The cells were washed three times with cold PBS and lysed (0.2 M NaOH, 0.05% SDS). Cell lysates were mixed with Ultima Gold liquid scintillation solution (Perkin Elmer, Rodgau, Germany) and the radioactivity measured in a liquid scintillation counter (Packard Instruments, Frankfurt, Germany).

4. HBV Infection Inhibition Assay

HepG2 NTCP cells seeded in a 24 well format were preincubated with the indicated peptide at indicated concentrations for 30 min at 37° C. in culture medium. The cells were subsequently infected with HBV (GE 1.8×10$^{8}$) overnight in cell culture medium containing 4% PEG for 16 h at 37° C. in the presence of the peptides followed by a washing step with PBS. The medium was changed every two days and supernatant collected from day 5 to 7 post infection for HBeAg measurement.

The features disclosed in the foregoing description, in the claims and/or in the accompanying drawings may, both separately and in any combination thereof, be material for realizing the invention in diverse forms thereof.

REFERENCES

Chan, H L. & Sung, J J. Hepatocellular carcinoma and hepatitis B virus. *Semin Liver Dis* 26, 153-161 (2006).

Cho M H, Song J S, Kim H J, Park S G, Jung G. Structure-based design and biochemical evaluation of sulfanilamide derivatives as hepatitis B virus capsid assembly inhibitors. *J Enzyme Inhib Med Chem* 2013; 28:916-925.

Dawson S, et al. (2012) In vitro inhibition of the bile salt export pump correlates with risk of cholestatic drug-induced liver injury in humans. *Drug Metab Dispos* 40: 130-138.

Doring B, Lutteke T, Geyer J, Petzinger E. The SLC10 carrier family: transport functions and molecular structure. *Curr Top Membr* 2012; 70:105-168.

Fattinger K, Funk C, Pantze M, et al. The endothelin antagonist bosentan inhibits the canalicular bile salt export pump: a potential mechanism for hepatic adverse reactions. *Clin Pharmacol Ther.* 2001; 69:223-31.

Funk C, Pantze M, Jehle L, et al. Troglitazone-induced intrahepatic cholestasis by an interference with the hepatobiliary export of bile acids in male and female rats. Correlation with the gender difference in troglitazone sulfate formation and the inhibition of the canalicular bile salt export pump (Bsep) by troglitazone and troglitazone sulfate. *Toxicology.* 2001; 167:83-98.

Funk C, Ponelle C, Scheuermann G, et al. Cholestatic potential of troglitazone as a possible factor contributing to troglitazone-induced hepatotoxicity: in vivo and in vitro interaction at the canalicular bile salt export pump (Bsep) in the rat. *Mol Pharmacol.* 2001; 59:627-35.

Gausepohl, H. et al. *Int. J. Prot. Pept. Res.* 34, 287-294 (1989).

Gripon P, Cannie I, Urban S. Efficient inhibition of hepatitis B virus infection by acylated peptides derived from the large viral surface protein. *J Virol* 2005; 79:1613-1622.

Kotani N, Maeda K, Debori Y, Camus S, Li R, Chesne C, Sugiyama Y. Expression and Transport Function of Drug Uptake Transporters in Differentiated HepaRG Cells. *Mol Pharm* 2012; 9(12):3434-41.

Lempp F A, Urban S. Inhibitors of hepatitis B virus attachment and entry. *Intervirology* 2014; 57:151-157.

Mailly L, Xiao F, Lupberger J, Wilson G K, Aubert P, Duong F H, Calabrese D, Leboeuf C, Fofana I, Thumann C, Bandiera S, Litgehetmann M, Volz T, Davis C, Harris H J, Mee C J, Girardi E, Chane-Woon-Ming B, Ericsson M, Fletcher N, Bartenschlager R, Pessaux P, Vercauteren K, Meuleman P, Villa P, Kaderali L, Pfeffer S, Heim M H, Neunlist M, Zeisel M B, Dandri M, McKeating J A, Robinet E, Baumert T F. Clearance of persistent hepatitis C virus infection in humanized mice using a claudin-1-targeting monoclonal antibody. *Nat Biotechnol.* 2015; 33(5):549-54. doi: 10.1038/nbt.3179. Epub 2015 Mar. 23.

Meier A, Mehrle S, Weiss T S, Mier W, Urban S. The myristoylated preS1-domain of the Hepatitis B Virus L-protein mediates specific binding to differentiated hepatocytes. *Hepatology* 2012; 58:31-42.

Mitchell A R, Erickson B W, Ryabtsev M N, Hodges R S, and Merrifield R B, Tert-butoxycarbonylaminoacyl-4-(oxymethyl)-phenylacetamidomethyl-resin, a more acid-resistant support for solid-phase peptide synthesis. *J Am Chem Soc.* 1976; 98(23):7357-62.

Morgan R E, et al. (2010) Interference with bile salt export pump function is a susceptibility factor for human liver injury in drug development. *Toxicol Sci* 118: 485-500.

Muiller T, Mehrle S, Schieck A, Haberkorn U, Urban S, Mier W. Liver imaging with a novel hepatitis B surface protein derived SPECT-tracer. *Mol Pharm.* 2013; 10(6): 2230-6.

Ni Y, Lempp F A, Mehrle S, Nkongolo S, Kaufman C, Falth M, Stindt J, et al. Hepatitis B and D Viruses Exploit Sodium Taurocholate Co-transporting Polypeptide for Species-Specific Entry into Hepatocytes. *Gastroenterology* 2014; 146:1070-1083.

Ogimura E, et al. (2011) Bile salt export pump inhibitors are associated with bile acid-dependent drug-induced toxicity in sandwich-cultured hepatocytes. *Biochem Biophys Res Commun* 416: 313-317.

Schieck A, Müller T, Schulze A, Haberkorn U, Urban S and Mier W. Solid-Phase Synthesis of the Lipopeptide Myr-HBVpreS/2-78, a Hepatitis B Virus Entry Inhibitor. *Molecules* 2010, 15(7), 4773-4783.

Schieck A, Schulze A, Gahler C, Muller T, Haberkorn U, Alexandrov A, Urban S, Mier W. Hepatitis B virus hepatotropism is mediated by specific receptor recognition in the liver and not restricted to susceptible hosts. *Hepatology* 2013; 58(1): 43-53. [Epub ahead of print: 2013 Jan. 4.]

Schulze A, Schieck A, Ni Y, Mier W, Urban S. Fine mapping of pre-S sequence requirements for hepatitis B virus large envelope protein-mediated receptor interaction. *J Virol* 2010; 84:1989-2000.

Shepard, C. W., Simard, E. P., Finelli, L., Fiore, A. E. & Bell, B. P. Hepatitis B virus infection: epidemiology and vaccination. *Epidemiol Rev* 28, 112-125 (2006).

Slijepcevic, D., Kaufman, C., Wichers, C. G. K., Gilglioni, E. H., Lempp, F. A., Duijst, S., de Waart, D. R., Oude Elferink, R. P. J., Mier, W., Stieger, B., Beuers, U., Urban, S., van de Graaf, S. F. J., 2015. Impaired uptake of conjugated bile acids and hepatitis b virus pres1-binding in na+-taurocholate cotransporting polypeptide knockout mice. *Hepatology* 62, 207-219

Stieger B, Fattinger K, Madon J, et al. Drug- and estrogen-induced cholestasis through inhibition of the hepatocellular bile salt export pump (Bsep) of rat liver. *Gastroenterology.* 2000; 118:422-30.

Stray S J, Zlotnick A. BAY 41-4109 has multiple effects on Hepatitis B virus capsid assembly. *J Mol Recognit* 2006; 19:542-548.

Urban S, Future *Virol.* 2008, 3(3), 253-264.

Urban S, Bartenschlager R, Kubitz R, Zoulim F. Strategies to Inhibit Entry of HBV and HDV into Hepatocytes. Gastroenterology 2014; 147(1):48-64.

Wang Y J, Lu D, Xu Y B, Xing W Q, Tong X K, Wang G F, et al. A Novel Pyridazinone Derivative Inhibits Hepatitis B Virus Replication by Inducing Genome-Free Capsid Formation. *Antimicrobial agents and chemotherapy* 2015; 59:7061-7072.

White C J and Yudin A K. Contemporary strategies for peptide macrocyclization, *Nature Chemistry* 2011; 3, 509-524.

Yan H, Zhong G, Xu G, He W, Jing Z, Gao Z, Huang Y, et al. Sodium taurocholate cotransporting polypeptide is a functional receptor for human hepatitis B and D virus. *elife.* 2012; 1:e00049.

Zoulim, F. Antiviral therapy of chronic hepatitis B. *Antiviral Res* 71, 206-215 (2006).

---

The invention claimed is:

1. A peptide comprising the amino acid sequence selected from

| | |
|---|---|
| cyclo[PNPLGFFPDH] | (SEQ. ID NO: 9) |
| cyclo[NPLGFFPDH] | (SEQ. ID NO: 12) |
| cyclo[PNPLGFFPDH] | (SEQ. ID NO: 15) |
| cyclo[PNPLGFLPD] | (SEQ. ID NO: 28) |
| cyclo[NPLGFLPDH] | (SEQ. ID NO: 29) |
| cyclo[PNPLGFLPDH] | (SEQ. ID NO: 30) |
| cyclo[GTNLSVPNPLGFLPDHQLDP], | (SEQ. ID NO: 31) | wherein the peptide carries at least one hydrophobic modification, which an acylation with a C8 to C22 fatty acid and/or addition of hydrophobic moieties, or a pharmaceutically acceptable salt thereof.

2. The peptide of claim 1, wherein the peptide is cyclized
   (a) via thiol oxidation of two cysteines in the peptide,
   (b) amide condensation of two amino acid side chains,
   (c) via head-to-tail cyclization,
   (d) via backbone cyclization,
   (e) via thioether formation,
   and/or
   (f) via hydrogen bond formation and/or bond-forming derivatives of amino acids.

3. The peptide of claim 1, further comprising an accessory domain, which is part of the cyclic peptide or is acyclic.

4. The peptide of claim 1, wherein the peptide consists of the amino acid sequence selected from:

| | | |
|---|---|---|
| HBVpreS9-16 | NPLGFFPD | (SEQ ID NO: 6) |
| HBVpreS8-16 | PNPLGFFPD | (SEQ ID NO: 9) |
| HBVpreS9-1 | NPLGFFPDH | (SEQ ID NO: 12) |
| HBVpreS8-17 | PNPLGFFPDH | (SEQ ID NO: 15) |

5. The peptide of claim 1, comprising one or more further moieties,
selected from
drugs and their respective prodrugs;
tags;
labels;
recombinant viruses and derivatives thereof;
carrier or depots for drugs, prodrugs or labels;
immunogenic epitopes;
hormones;
inhibitors; and
toxins.

6. A pharmaceutical composition comprising:
   (i) at least one peptide of claim 1, and
   (ii) optionally, a pharmaceutically acceptable carrier and/ or excipient.

7. The peptide, according to claim 1, wherein the peptide consists of the amino acid sequence selected from

```
                                          (SEQ. ID NO: 9)
    Myr-cyclo (myr-cyclo[PNPLGFFPD])

(SEQ. ID NO: 12)
    Myr-cyclo (myr-cyclo[NPLGFFPDH])
    and (SEQ. ID NO: 15)
    Myr-cyclo (myr-cyclo[PNPLGFFPDH]).
```

8. The peptide, according to claim 1, wherein the peptide consists of the amino acid sequence selected from

```
                                          (SEQ. ID NO: 9)
    cyclo[PNPLGFFPD]

(SEQ. ID NO: 12)
    cyclo[NPLGFFPDH]

(SEQ. ID NO: 15)
    cyclo[PNPLGFFPDH]

(SEQ ID NO. 28)
    cyclo[PNPLGFLPD]

(SEQ ID NO. 29)
    cyclo[NPLGFLPDH]

(SEQ ID NO. 30)
    cyclo[PNPLGFLPDH]
    and (SEQ ID NO. 31)
    cyclo[GTNLSVPNPLGFLPDHQLDP].
```

* * * * *

SEQUENCE LISTING

```
<160> NUMBER OF SEQ ID NOS: 46

<210> SEQ ID NO 1
<211> LENGTH: 7
<212> TYPE: PRT
<213> ORGANISM: Artificial Sequence
<220> FEATURE:
<223> OTHER INFORMATION: Essential domain or pharmacophore, amino acid
      sequence P, with Xaa = F or L
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Asn Pro Leu Gly Phe Xaa Pro
1               5

<210> SEQ ID NO 2
<211> LENGTH: 7
<212> TYPE: PRT
<213> ORGANISM: Hepatitis B virus

<400> SEQUENCE: 2

Asn Pro Leu Gly Phe Phe Pro
1               5

<210> SEQ ID NO 3
<211> LENGTH: 7
<212> TYPE: PRT
<213> ORGANISM: Artificial Sequence
<220> FEATURE:
<223> OTHER INFORMATION: Essential domain or pharmacophore, amino acid
      sequence P with Xaa = L

<400> SEQUENCE: 3

Asn Pro Leu Gly Phe Leu Pro
```

```
<210> SEQ ID NO 4
<211> LENGTH: 9
<212> TYPE: PRT
<213> ORGANISM: Artificial Sequence
<220> FEATURE:
<223> OTHER INFORMATION: Cys-preS9-15-Cys

<400> SEQUENCE: 4

Cys Asn Pro Leu Gly Phe Phe Pro Cys
1               5

<210> SEQ ID NO 5
<211> LENGTH: 10
<212> TYPE: PRT
<213> ORGANISM: Artificial Sequence
<220> FEATURE:
<223> OTHER INFORMATION: Cys-HBVpreS9-15-Cys-D-Tyr

<400> SEQUENCE: 5

Cys Asn Pro Leu Gly Phe Phe Pro Cys Tyr
1               5                   10

<210> SEQ ID NO 6
<211> LENGTH: 8
<212> TYPE: PRT
<213> ORGANISM: Hepatitis B virus

<400> SEQUENCE: 6

Asn Pro Leu Gly Phe Phe Pro Asp
1               5

<210> SEQ ID NO 7
<211> LENGTH: 10
<212> TYPE: PRT
<213> ORGANISM: Artificial Sequence
<220> FEATURE:
<223> OTHER INFORMATION: Cys-HBVpreS9-16-Cys

<400> SEQUENCE: 7

Cys Asn Pro Leu Gly Phe Phe Pro Asp Cys
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Cys-HBVpreS9-16-Cys-D-Tyr

<400> SEQUENCE: 8

Cys Asn Pro Leu Gly Phe Phe Pro Asp Cys Tyr
1               5                   10

<210> SEQ ID NO 9
<211> LENGTH: 9
<212> TYPE: PRT
<213> ORGANISM: Hepatitis B virus

<400> SEQUENCE: 9

Pro Asn Pro Leu Gly Phe Phe Pro Asp
1               5

<210> SEQ ID NO 10
<211> LENGTH: 11
```

```
<212> TYPE: PRT
<213> ORGANISM: Artificial Sequence
<220> FEATURE:
<223> OTHER INFORMATION: Cys-HBVpreS8-16-Cys

<400> SEQUENCE: 10

Cys Pro Asn Pro Leu Gly Phe Phe Pro Asp Cys
1               5                   10

<210> SEQ ID NO 11
<211> LENGTH: 12
<212> TYPE: PRT
<213> ORGANISM: Artificial Sequence
<220> FEATURE:
<223> OTHER INFORMATION: Cys-HBVpreS8-16-Cys-D-Tyr

<400> SEQUENCE: 11

Cys Pro Asn Pro Leu Gly Phe Phe Pro Asp Cys Tyr
1               5                   10

<210> SEQ ID NO 12
<211> LENGTH: 9
<212> TYPE: PRT
<213> ORGANISM: Hepatitis B virus

<400> SEQUENCE: 12

Asn Pro Leu Gly Phe Phe Pro Asp His
1               5

<210> SEQ ID NO 13
<211> LENGTH: 11
<212> TYPE: PRT
<213> ORGANISM: Artificial Sequence
<220> FEATURE:
<223> OTHER INFORMATION: Cys-HBVpreS9-17-Cys

<400> SEQUENCE: 13

Cys Asn Pro Leu Gly Phe Phe Pro Asp His Cys
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Cys-HBVpreS9-17-Cys-D-Tyr

<400> SEQUENCE: 14

Cys Asn Pro Leu Gly Phe Phe Pro Asp His Cys Tyr
1               5                   10

<210> SEQ ID NO 15
<211> LENGTH: 10
<212> TYPE: PRT
<213> ORGANISM: Hepatitis B virus

<400> SEQUENCE: 15

Pro Asn Pro Leu Gly Phe Phe Pro Asp His
1               5                   10

<210> SEQ ID NO 16
<211> LENGTH: 12
<212> TYPE: PRT
<213> ORGANISM: Artificial Sequence
<220> FEATURE:
<223> OTHER INFORMATION: Cys-HBVpreS8-17-Cys
```

```
<400> SEQUENCE: 16

Cys Pro Asn Pro Leu Gly Phe Phe Pro Asp His Cys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Cys-HBVpreS8-17-Cys-D-Tyr

<400> SEQUENCE: 17

Cys Pro Asn Pro Leu Gly Phe Phe Pro Asp His Cys Tyr
1               5                   10

<210> SEQ ID NO 18
<211> LENGTH: 20
<212> TYPE: PRT
<213> ORGANISM: Hepatitis B virus

<400> SEQUENCE: 18

Gly Thr Asn Leu Ser Val Pro Asn Pro Leu Gly Phe Phe Pro Asp His
1               5                   10                  15

Gln Leu Asp Pro
            20

<210> SEQ ID NO 19
<211> LENGTH: 22
<212> TYPE: PRT
<213> ORGANISM: Artificial Sequence
<220> FEATURE:
<223> OTHER INFORMATION: Cys-HBVpreS2-21-Cys

<400> SEQUENCE: 19

Cys Gly Thr Asn Leu Ser Val Pro Asn Pro Leu Gly Phe Phe Pro Asp
1               5                   10                  15

His Gln Leu Asp Pro Cys
            20

<210> SEQ ID NO 20
<211> LENGTH: 23
<212> TYPE: PRT
<213> ORGANISM: Artificial Sequence
<220> FEATURE:
<223> OTHER INFORMATION: Cys-HBVpreS2-21-Cys-D-Tyr

<400> SEQUENCE: 20

Cys Gly Thr Asn Leu Ser Val Pro Asn Pro Leu Gly Phe Phe Pro Asp
1               5                   10                  15

His Gln Leu Asp Pro Cys Tyr
            20

<210> SEQ ID NO 21
<211> LENGTH: 47
<212> TYPE: PRT
<213> ORGANISM: Hepatitis B virus

<400> SEQUENCE: 21

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
```

-continued

```
              35                  40                  45

<210> SEQ ID NO 22
<211> LENGTH: 49
<212> TYPE: PRT
<213> ORGANISM: Artificial Sequence
<220> FEATURE:
<223> OTHER INFORMATION: Cys-HBVpreS2-48-Cys

<400> SEQUENCE: 22

Cys Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30

Asp Phe Asn Pro Asn Lys Asp His Trp Pro Glu Ala Asn Gln Val Gly
        35                  40                  45

Cys

<210> SEQ ID NO 23
<211> LENGTH: 50
<212> TYPE: PRT
<213> ORGANISM: Artificial Sequence
<220> FEATURE:
<223> OTHER INFORMATION: Cys-HBVpreS2-48-Cys-D-Tyr

<400> SEQUENCE: 23

Cys Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30

Asp Phe Asn Pro Asn Lys Asp His Trp Pro Glu Ala Asn Gln Val Gly
        35                  40                  45

Cys Tyr
    50

<210> SEQ ID NO 24
<211> LENGTH: 47
<212> TYPE: PRT
<213> ORGANISM: Artificial Sequence
<220> FEATURE:
<223> OTHER INFORMATION: amino acid residues of Myrcludex B

<400> SEQUENCE: 24

Gly Thr Asn Leu Ser Val Pro Asn Pro Leu Gly Phe Phe Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 25
<211> LENGTH: 49
<212> TYPE: PRT
<213> ORGANISM: Artificial Sequence
<220> FEATURE:
<223> OTHER INFORMATION: Cys-Myrcludex B-Cys

<400> SEQUENCE: 25

Cys Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30
```

Asp Phe Asn Pro Asn Lys Asp His Trp Pro Glu Ala Asn Lys Val Gly
        35                  40                  45

Cys

<210> SEQ ID NO 26
<211> LENGTH: 50
<212> TYPE: PRT
<213> ORGANISM: Artificial Sequence
<220> FEATURE:
<223> OTHER INFORMATION: Cys- Myrcludex B-Cys-D-Tyr

<400> SEQUENCE: 26

Cys Gly Thr Asn Leu Ser Val Pro Asn Pro Leu Gly Phe Phe Pro Asp
1               5                   10                  15

His Gln Leu Asp Pro Ala Phe Gly Ala Asn Ser Asn Asn Pro Asp Trp
            20                  25                  30

Asp Phe Asn Pro Asn Lys Asp His Trp Pro Glu Ala Asn Lys Val Gly
        35                  40                  45

Cys Tyr
    50

<210> SEQ ID NO 27
<211> LENGTH: 8
<212> TYPE: PRT
<213> ORGANISM: Artificial Sequence
<220> FEATURE:
<223> OTHER INFORMATION: HBVpreS9-16 with Xaa = L

<400> SEQUENCE: 27

Asn Pro Leu Gly Phe Leu Pro Asp
1               5

<210> SEQ ID NO 28
<211> LENGTH: 9
<212> TYPE: PRT
<213> ORGANISM: Artificial Sequence
<220> FEATURE:
<223> OTHER INFORMATION: HBVpreS8-16 with Xaa = L

<400> SEQUENCE: 28

Pro Asn Pro Leu Gly Phe Leu Pro Asp
1               5

<210> SEQ ID NO 29
<211> LENGTH: 9
<212> TYPE: PRT
<213> ORGANISM: Artificial Sequence
<220> FEATURE:
<223> OTHER INFORMATION: HBVpreS9-17 with Xaa = L

<400> SEQUENCE: 29

Asn Pro Leu Gly Phe Leu Pro Asp His
1               5

<210> SEQ ID NO 30
<211> LENGTH: 10
<212> TYPE: PRT
<213> ORGANISM: Artificial Sequence
<220> FEATURE:
<223> OTHER INFORMATION: HBVpreS8-17 with Xaa = L

<400> SEQUENCE: 30

Pro Asn Pro Leu Gly Phe Leu Pro Asp His
1               5                   10

```
<210> SEQ ID NO 31
<211> LENGTH: 20
<212> TYPE: PRT
<213> ORGANISM: Artificial Sequence
<220> FEATURE:
<223> OTHER INFORMATION: HBVpreS2-21 with Xaa = L

<400> SEQUENCE: 31

Gly Thr Asn Leu Ser Val Pro Asn Pro Leu Gly Phe Leu Pro Asp His
1               5                   10                  15

Gln Leu Asp Pro
            20

<210> SEQ ID NO 32
<211> LENGTH: 47
<212> TYPE: PRT
<213> ORGANISM: Artificial Sequence
<220> FEATURE:
<223> OTHER INFORMATION: HBVpreS2-48 with Xaa = L

<400> SEQUENCE: 32

Gly Thr Asn Leu Ser Val Pro Asn Pro Leu Gly Phe Leu Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Gln Val Gly
        35                  40                  45

<210> SEQ ID NO 33
<211> LENGTH: 47
<212> TYPE: PRT
<213> ORGANISM: Artificial Sequence
<220> FEATURE:
<223> OTHER INFORMATION: amino acid residues of Myrcludex B with Xaa = L

<400> SEQUENCE: 33

Gly Thr Asn Leu Ser Val Pro Asn Pro Leu Gly Phe Leu Pro Asp His
1               5                   10                  15

Gln Leu Asp Pro Ala Phe Gly Ala Asn Ser Asn Asn Pro Asp Trp Asp
            20                  25                  30

Phe Asn Pro Asn Lys Asp His Trp Pro Glu Ala Asn Lys Val Gly
        35                  40                  45

<210> SEQ ID NO 34
<211> LENGTH: 119
<212> TYPE: PRT
<213> ORGANISM: Hepatitis B virus

<400> SEQUENCE: 34

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Gln Ala Asn Gln Val Gly Val Gly Ala Phe Gly
    50                  55                  60

Pro Gly Phe Thr Pro Pro His Gly Gly Val Leu Gly Trp Ser Pro Gln
65                  70                  75                  80

Ala Gln Gly Ile Leu Ala Thr Val Pro Ala Met Pro Pro Pro Ala Ser
```

85                  90                  95

Thr Asn Arg Gln Ser Gly Arg Gln Pro Thr Pro Ile Ser Pro Pro Leu
            100                 105                 110

Arg Asp Ser His Pro Gln Ala
            115

<210> SEQ ID NO 35
<211> LENGTH: 119
<212> TYPE: PRT
<213> ORGANISM: Hepatitis B virus

<400> SEQUENCE: 35

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala
            115

<210> SEQ ID NO 36
<211> LENGTH: 119
<212> TYPE: PRT
<213> ORGANISM: Hepatitis B virus

<400> SEQUENCE: 36

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Ser Val Pro Ala Ala Pro Pro Pro Ala Ser
                85                  90                  95

Thr Asn Arg Gln Ser Gly Arg Gln Pro Thr Pro Leu Ser Pro Pro Leu
            100                 105                 110

Arg Asp Thr His Pro Gln Ala
            115

<210> SEQ ID NO 37
<211> LENGTH: 108
<212> TYPE: PRT
<213> ORGANISM: Hepatitis B virus

<400> SEQUENCE: 37

```
Met Gly Gln Asn Leu Ser Thr Ser Asn Pro Leu Gly Phe Phe Pro Glu
1               5                   10                  15

His Gln Leu Asp Pro Ala Phe Lys Ala Asn Thr Asn Pro Asp Trp
            20                  25                  30

Asp Phe Asn Pro Lys Lys Asp Tyr Trp Pro Glu Ala Asn Lys Val Gly
                35                  40                  45

Ala Gly Ala Phe Gly Pro Gly Phe Thr Pro His Gly Gly Leu Leu
    50                  55                  60

Gly Trp Ser Pro Gln Ala Gln Gly Ile Leu Thr Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asp Thr His Pro Gln Ala
                100                 105
```

<210> SEQ ID NO 38
<211> LENGTH: 107
<212> TYPE: PRT
<213> ORGANISM: Hepatitis B virus

<400> SEQUENCE: 38

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Asn Pro Asp Trp
            20                  25                  30

Asp Phe Asn Pro Asn Lys Asp Thr Trp Pro Asp Ala Asn Lys Val Gly
                35                  40                  45

Ala Gly Ala Phe Gly Leu Gly Phe Thr Pro Pro His Gly Gly Leu Leu
    50                  55                  60

Gly Trp Ser Pro Gln Ala Gln Gly Phe Gln Thr Leu Pro Ala Asn Pro
65                  70                  75                  80

Pro Pro Ala Ser Thr Asn Arg Gln Ser Gly Arg Gln Pro Thr Pro Leu
                85                  90                  95

Ser Pro Pro Leu Arg Thr Thr His Pro Gln Ala
                100                 105
```

<210> SEQ ID NO 39
<211> LENGTH: 118
<212> TYPE: PRT
<213> ORGANISM: Hepatitis B virus

<400> SEQUENCE: 39

```
Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
                35                  40                  45

Asp His Trp Thr Glu Ala Asn Lys Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Pro Leu Arg
                100                 105                 110
```

Asp Thr His Pro Gln Ala
        115

<210> SEQ ID NO 40
<211> LENGTH: 119
<212> TYPE: PRT
<213> ORGANISM: Hepatitis B virus

<400> SEQUENCE: 40

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Ser Trp Pro Met Ala Asn Lys Val Gly Val Gly Gly Tyr Gly
    50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala
        115

<210> SEQ ID NO 41
<211> LENGTH: 118
<212> TYPE: PRT
<213> ORGANISM: Hepatitis B virus

<400> SEQUENCE: 41

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45

Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala
        115

<210> SEQ ID NO 42
<211> LENGTH: 108
<212> TYPE: PRT
<213> ORGANISM: Hepatitis B virus

<400> SEQUENCE: 42

Met Gly Gln Asn His Ser Val Thr Asn Pro Leu Gly Phe Phe Pro Asp
1               5                   10                  15

```
His Gln Leu Asp Pro Leu Phe Arg Ala Asn Ser Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Ala
65                  70                  75                  80

Pro Pro Pro Ala Ser Thr Asn Arg Gln Ser Gly Arg Lys Ala Thr Pro
                85                  90                  95

Ile Ser Pro Pro Leu Arg Asp Thr His Pro Gln Ala
                100                 105

<210> SEQ ID NO 43
<211> LENGTH: 119
<212> TYPE: PRT
<213> ORGANISM: Hepatitis B virus

<400> SEQUENCE: 43

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
                100                 105                 110

Arg Asp Thr His Pro Gln Ala
        115

<210> SEQ ID NO 44
<211> LENGTH: 108
<212> TYPE: PRT
<213> ORGANISM: Hepatitis B virus

<400> SEQUENCE: 44

Met Gly Gln Asn Leu Ser Val Ser Asn Pro Leu Gly Phe Phe Pro Glu
1               5                   10                  15

His Gln Leu Asp Pro Leu Phe Arg Ala Asn Thr Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Val Thr Thr Ile Leu Pro Ala Val
65                  70                  75                  80

Pro Pro Pro Ala Ser Thr Asn Arg Gln Ser Gly Arg Gln Pro Thr Pro
                85                  90                  95

Ile Ser Pro Pro Leu Arg Asp Thr His Pro Gln Ala
                100                 105
```

```
<210> SEQ ID NO 45
<211> LENGTH: 105
<212> TYPE: PRT
<213> ORGANISM: Hepatitis B virus

<400> SEQUENCE: 45

Met Gly Leu Asn Gln Ser Thr Phe Pro Leu Gly Phe Phe Pro Ser His
1               5                   10                  15

Gln Leu Asp Pro Leu Phe Lys Ala Asn Ala Gly Ser Ala Asp Trp Asp
            20                  25                  30

Lys Pro Lys Asp Pro Trp Pro Gln Ala His Asp Thr Ala Val Gly Ala
        35                  40                  45

Phe Gly Pro Gly Leu Val Pro Pro His Gly Gly Leu Leu Gly Trp Ser
50                  55                  60

Ser Gln Ala Gln Gly Leu Ser Val Thr Val Pro Asp Thr Pro Pro Pro
65                  70                  75                  80

Pro Ser Thr Asn Arg Asp Lys Gly Arg Lys Pro Thr Pro Ala Thr Pro
                85                  90                  95

Pro Leu Arg Asp Thr His Pro Gln Ala
                100                 105

<210> SEQ ID NO 46
<211> LENGTH: 59
<212> TYPE: PRT
<213> ORGANISM: Artificial Sequence
<220> FEATURE:
<223> OTHER INFORMATION: HBV preS consensus sequence (for amino acid
      positions (-11) to 48)

<400> SEQUENCE: 46

Met Gly Gly Trp Ser Ser Thr Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Arg Ala Asn Ser Asn Asn Pro Asp Trp Asp Phe Asn Pro Asn
        35                  40                  45

Lys Asp His Trp Pro Glu Ala Asn Lys Val Gly
    50                  55
```